US008633013B2

(12) United States Patent
Kaiser et al.

(10) Patent No.: US 8,633,013 B2
(45) Date of Patent: Jan. 21, 2014

(54) ASSAYS

(75) Inventors: Thomas Kaiser, Hohlstedt (DE); Klaus-Peter Möbius, Zöllnitz (DE); Torsten Schulz, Jena (DE); Thomas Uhlig, Jena (DE); Alexander Von Schenk Zu Schweinsberg, Jena (DE); Eugen Ermantraut, Jena (DE); Jens Tuchscheerer, Jena (DE)

(73) Assignee: Clondiag GmbH, Jena (DE)

( * ) Notice: Subject to any disclaimer, the term of this patent is extended or adjusted under 35 U.S.C. 154(b) by 680 days.

(21) Appl. No.: 12/451,243

(22) PCT Filed: May 5, 2008

(86) PCT No.: PCT/EP2008/055508

§ 371 (c)(1), (2), (4) Date: Mar. 26, 2010

(87) PCT Pub. No.: WO2008/135564

PCT Pub. Date: Nov. 13, 2008

(65) Prior Publication Data

US 2010/0179068 A1 Jul. 15, 2010

Related U.S. Application Data

(60) Provisional application No. 61/036,537, filed on Mar. 14, 2008, provisional application No. 60/915,884, filed on May 3, 2007.

(51) Int. Cl.
*C12M 1/34* (2006.01)

(52) U.S. Cl.
USPC .................. 435/287.2; 435/288.4; 435/288.5; 422/414

(58) Field of Classification Search
None
See application file for complete search history.

(56) References Cited

U.S. PATENT DOCUMENTS

| | | | | |
|---|---|---|---|---|
| 5,910,288 | A * | 6/1999 | Schembri | 422/551 |
| 2003/0008308 | A1 | 1/2003 | Enzelberger et al. | |
| 2004/0248167 | A1 | 12/2004 | Quake et al. | |
| 2009/0079963 | A1 * | 3/2009 | Ermantraut et al. | 356/39 |

FOREIGN PATENT DOCUMENTS

| | | |
|---|---|---|
| EP | 1279436 | 1/2003 |
| WO | WO 02060582 | 8/2002 |
| WO | WO 03015923 | 2/2003 |
| WO | WO 2005/108604 | 5/2005 |
| WO | WO 2007/051861 | 5/2007 |

OTHER PUBLICATIONS

U.S. Appl. No. 60/826,678, filed Sep. 22, 2006, Ermantraut et al.

* cited by examiner

*Primary Examiner* — Chris L Chin
(74) *Attorney, Agent, or Firm* — Steptoe & Johnson LLP

(57) ABSTRACT

A method for assaying a sample for each of multiple analytes is described. The method includes contacting an array of spaced-apart test zones with a liquid sample (e.g., whole blood). The test zones disposed within a channel of a microfluidic device. The channel is defined by at least one flexible wall and a second wall which may or may not be flexible. Each test zone comprising a probe compound specific for a respective target analyte. The microfluidic device is compressed to reduce the thickness of the channel, which is the distance between the inner surfaces of the walls within the channel. The presence of each analyte is determined by optically detecting an interaction at each of multiple test zones for which the distance between the inner surfaces at the corresponding location is reduced. The interaction at each test zone is indicative of the presence in the sample of a target analyte.

18 Claims, 20 Drawing Sheets

400
402
404
d1
102 d2
404
402
102

400
d3
402
102

400
d3
402'
102 a2
402'
d3
102

400
d1
112
102

ASSAYS

CLAIM OF PRIORITY

This application claims priority under 35 USC 371 to International Application No. PCT/EP2008/055508, filed on May 5, 2008, which claims priority to U.S. Provisional Application Ser. No. 60/915,884, filed on May 3, 2007, which claims priority to U.S. Provisional Application Ser. No. 61/036,537, filed on Mar. 3, 2008, each of which is incorporated by reference in its entirety.

This application is related to U.S. provisional application 60/826,678 filed Sep. 22, 2006, to the U.S. continuation of International Patent Application PCT/EP2005/004923, filed May 6, 2005, which designates the United States and claims priority to German Patent Application DE 10 2004 022 263, filed May 6, 2004, the U.S. continuation having Ser. No. 11/593,021 and being filed Nov. 6, 2006, to International Patent Applications PCT/EP2006/068153, and EP06/068155, filed Nov. 6, 2006 which designates the United States and claims priority to German Patent Application DE 10 2005 052 752, filed Nov. 4, 2005, the international application being filed Nov. 6, 2006, and to U.S. provisional application 60/867,019 filed Nov. 22, 2006. Each of the foregoing applications is incorporated herein by reference.

FIELD OF THE INVENTION

The present invention relates to assays (e.g., assays for one or more analytes in a sample).

BACKGROUND

Assays can be performed to determine the presence of one or more analytes in a sample. Arrays can be used to perform multiple assays (e.g., for each of multiple different analytes) on a sample. Typical arrays include a substrate having multiple spaced apart test zones each having a different probe compound such as a polynucleotide, antibody, or protein. In use, the array is contacted with a sample, which then interacts with the sites of the array. For each site, the interaction can include, for example, binding of a corresponding analyte to probe compounds of the site and/or a chemical reaction between the corresponding analyte and the probe compounds. The reaction results in a detectable product (e.g., a precipitate). The presence and extent of interaction depends upon whether a corresponding analyte is present in the sample.

Typically, the interaction is detected optically (e.g., by fluorescence). For example, optical detection can be performed using an imaging detector (e.g., a CCD) having multiple light sensitive elements (e.g., pixels) spaced apart from one another in at least one (e.g., two) dimensions. Each of the light sensitive elements is positioned to receive light from a different spatial location of the substrate. Thus, light simultaneously detected by multiple light sensitive elements can be combined to form image data in at least one (e.g., two) dimensions of the substrate. The image data can be evaluated to determine the presence and/or extent of interaction at multiple sites of the array.

SUMMARY

The present invention relates to assays (e.g., assays for multiple analytes in a sample).

In one aspect a method comprises:

contacting an array of spaced-apart test zones with a liquid sample, the test zones being disposed between an inner surface of a first substrate and an inner surface of a second substrate of a microfluidic device, at least one of the substrates being flexible, each test zone comprising a probe compound configured to participate in an assay for a target analyte, reducing a distance between the inner surfaces of the first and second substrates at locations of corresponding to the test zones, and sequentially optically determining the presence of an interaction at each of multiple test zones for which the distance between the inner surfaces at the corresponding location is reduced, the interaction at each test zone being indicative of the presence in the sample of a target analyte.

The method can further comprise, for each of multiple test zones, determining the presence of a respective analyte based on the optically determined interaction.

For each of at least some of the test zones, the interaction at each of multiple test zones can be a binding reaction between the analyte and the probe compound of the test zone.

Optically determining can comprise detecting light from each of the test zones using a zero$^{th}$ order detector.

Detecting light from each of the test zones using a zero$^{th}$ order detector can consist essentially of detecting light with the zero$^{th}$ order detector.

The method can further comprise, for each of multiple locations for which the distance between the inner surfaces of the first and second substrates was reduced, subsequently increasing the distance between the inner surfaces after the step of optically determining at the test zone.

Reducing a distance can comprise sequentially reducing the distance between the inner surfaces of the first and second substrates at locations corresponding to the test zones. In this embodiment, the method can further comprise, for each of multiple locations for which the distance between the inner surfaces of the first and second substrates was reduced, subsequently increasing the distance between the inner surfaces after the step of optically detecting binding at the test zone.

Optically determining can comprise sequentially detecting the interaction at each of multiple test zones for which the distance between the inner surfaces at the corresponding location is reduced. In one embodiment, optically detecting comprises simultaneously detecting light from no more than a number N test zones, where $N \leq 5$ or $N \leq 3$ or $N=1$. Alternatively, optically determining comprises detecting light from each of the test zones using a zero$^{th}$ order detector. Detecting light from each of the test zones using a zero$^{th}$ order detector can consist essentially of detecting light with the zero$^{th}$ order detector.

Optically detecting can comprise translating the microfluidic device with respect to an optical detection zone of an optical detector used to perform the optical determining.

Reducing a distance comprises translating the microfluidic device with respect to a member that applies a compressive force to the microfluidic device. Translating the microfluidic device with respect to the member can comprise rotating at least a portion of the member.

Each test zone can be elongate and define a major axis. Further, translating the microfluidic device can comprise translating the device along a translation axis generally perpendicular to the major axis of each of multiple test zones. E.g., the translation axis and the major axis of multiple of the test zones are perpendicular to within 10° or less or even within 5° or less.

Further, the translation axis and the major axis of most or even of all of the test zones can be generally perpendicular.

The method can further comprise, during the step of translating, reading information contained in a reference code of the microfluidic device, and determining based on the read information a property of each of multiple test zones.

Determining can comprise determining, for each of multiple test zones, a value indicative of when the test zone is in a detection zone of an optical detector used to perform the optical detecting. Further, determining can comprise determining a physiochemical property of test zones of the microfluidic device. E.g., the physiochemical property is indicative of an analyte that can be determined by each of multiple test zones. Further, determining can comprise determining an identity of reagents stored within the microfluidic device prior to use.

A ratio of a length along the major axis to a width along a perpendicular dimension of the test zones can be at least 2.5 or even at least 5.

The step of optically detecting can be performed without first contacting the test zones with a liquid free of the sample after the step of contacting.

Optical determining can comprise exciting and detecting fluorescence from the test zones.

In another aspect, a method comprises:

contacting an array of spaced-apart test zones with a sample, the test zones being disposed between first and second surfaces, each test zone comprising a probe compound configured to participate in an assay for a respective analyte, reducing a distance between the inner surfaces at locations of corresponding to the test zones, and sequentially optically determining the result of the assay at each of multiple test zones for which the distance between the inner surfaces at the corresponding location is reduced.

The method can further comprise, for each of multiple test zones, determining the presence of a respective analyte based on the result of the assay.

For each of at least some of the test zones, the result of the assay can be indicative of a binding reaction between the analyte and the probe compound of the test zone.

Optically determining can comprise detecting light from each of the test zones using a zero$^{th}$ order detector.

Detecting light from each of the test zones using a zero$^{th}$ order detector can consist essentially of detecting light with the zero$^{th}$ order detector.

The method can further comprise, for each of multiple locations for which the distance between the inner surfaces was reduced, subsequently increasing the distance between the inner surfaces after the step of optically determining at the test zone.

Reducing a distance can comprise sequentially reducing the distance between the inner surfaces at locations corresponding to the test zones.

In another aspect, a system comprises:

a microfluidic device reader configured to receive a microfluidic device comprising an array of spaced-apart test zones, the test zones being disposed between an inner surface of a first substrate and an inner surface of a second substrate of the microfluidic device, at least one of the substrates being flexible, each test zone comprising a probe compound configured to participate in an assay for a target analyte, an optical detector configured to detect light from at least one of the test zones when the at least one test zone is in a detection zone of the microfluidic device, a translator configured to translate at least one of the microfluidic device and the detection zone of the optical detector relative to the other, a compressor configured to reduce a distance between the inner surfaces of the first and second substrates at locations corresponding to the detection zone of the optical device, a processor configured to receive a signal from the optical detector, the signal indicative of light detected from a test zone.

The system can be configured to simultaneously optically detect light from no more than a number N test zones, where $N \leq 5$, or $N \leq 3$, or $N=1$.

The detector can be a fluorescence detector.

In another aspect, an assay device comprises first and second substrates defining a channel therebetween, at least one of the substrates being flexible, the channel comprising an array of spaced-apart test zones, each test zone comprising a probe compound configured to participate in an assay for a target analyte.

In another aspect, an article of manufacture comprises:

a substrate, and multiple elongate test zones, each test zone comprising a respective probe compound configured to participate in an assay for a target analyte, each test zone defining a major axis and a width perpendicular thereto, and the major axes of the test zones being generally parallel.

In another aspect, a method comprises:

introducing a liquid sample to a bore of a capillary, and introducing at least a portion of the liquid sample into a microfluidic network of the microfluidic device by reducing a pressure acting on a liquid sample-gas interface of the liquid sample.

The method can further comprise, subsequent to the step of introducing the liquid sample to the bore of the capillary, connecting the capillary to a microfluidic device, the liquid sample remaining within the capillary.

The reducing a pressure can be performed by compressing at least a portion of the microfluidic network to displace gas therefrom and subsequently decompressing the at least a portion of the microfluidic network.

The microfluidic network can be at least in part defined by and between first and second generally planar substrates, at least one of the substrates being deformable upon the application of external pressure to compress the at least a portion of the microfluidic network and the at least one substrate tending to resume its previous position upon release of the external pressure to permit decompression of the at least a portion of the microfluidic network.

Further, the microfluidic network can be at least in part defined by a microfluidic channel including an inlet and a detection region in fluid communication with the inlet, and a microfluidic flow path in fluid communication with the detection region, wherein the microfluidic flow path has a wall being at least partially deformable upon the application of external pressure to compress the at least a portion of the microfluidic flow path, and the wall tends to resume its previous position upon release of the external pressure to permit decompression of the at least a portion of the microfluidic flow path.

The method can further comprise combining the liquid sample with the one or more reagents present within the microfluidic network to form a mixture. The mixture can comprise at least 90% of the liquid sample that was introduced to the microfluidic network. The one or more reagents include a detectable label that react with the sample to form a complex including the label and an analyte present in the sample.

The method can further comprise optically detecting a signal indicative of an amount of complex present within a subset of the liquid sample, the subset being present within a detection zone of the microfluidic device.

The method can further comprise displacing the subset of liquid sample from the detection zone and introducing a different subset of the liquid sample into the detection zone and optically detecting a signal indicative of an amount of complex present within the different subset. Displacing the subset and introducing the different subset can be performed by compressing at least a portion of the microfluidic network, the compressed portion being at least partially offset along the network from the detection zone. Compressing the at least a portion can comprise compressing a first portion of the microfluidic network and, without first completely releasing the compression, moving a site of the compression along the microfluidic network by an amount sufficient to perform the steps of displacing and introducing.

The method can further comprise performing the step of optically detecting a signal indicative of an amount of complex present within the different subset without first completely releasing the compression of the microfluidic network.

The method can further comprise, intermediate the steps of introducing the liquid sample to the bore of the capillary and introducing at least the portion of the liquid sample into the microfluidic network, stopping the liquid sample from exiting the capillary. Stopping the liquid sample from exiting the capillary can comprise increasing the pressure acting on the liquid sample-gas interface.

In some embodiments, the microfluidic network does not support capillary flow of the liquid sample. An interior surface of the microfluidic network that is defined by at least one of the first and second substrates can be hydrophobic.

The analyte can be a particle, e.g., a cell.

The method can further comprise moving at least one of the microfluidic device and an optical detector with respect to one another and subsequently detecting an optical signal indicative of an amount of complex present within a different subset of the liquid sample.

The capillary can be an end to end capillary comprising first and second open ends, the bore of the capillary comprises a total volume V, and the step of introducing at least a portion of the liquid sample comprises introducing at least 90% of the liquid sample into the microfluidic network.

In another aspect, a method comprises:

introducing a liquid sample to a microfluidic network disposed between an inner surface of a first substrate and an inner surface of a second substrate of a microfluidic device, at least one of the substrates being flexible, the liquid sample comprising multiple particles, forming a mixture comprising at least a portion of the liquid sample and an optical label by sequentially reducing a distance between the inner surfaces of the first and second substrates at multiple positions within the microfluidic network, forming multiple complexes, each complex comprising one of the multiple particles and at least one of the optical labels, and detecting complexes present within a subset of the mixture.

The method can further comprise detecting complexes present within each of multiple different subsets of the mixture.

A total volume of the multiple different subsets can be at least 90% of a volume of the liquid sample introduced to the microfluidic device.

The method can further comprise introducing a total volume V of liquid sample to the microfluidic device and wherein a total volume of the mixture is at least 90% of the volume V.

The method can further comprise detecting complexes present within at least 90% of the total volume of the mixture.

The particles can be cells.

The optical labels can be fluorescent labels.

In another aspect, a method comprises:

introducing a total volume V of a liquid sample to a microfluidic network disposed between an inner surface of a first substrate and an inner surface of a second substrate of a microfluidic device, at least one of the substrates being flexible, the liquid sample comprising multiple particles, forming a mixture within the microfluidic network, the mixture comprising at least about 90% of the volume V of liquid sample and an optical label, forming multiple complexes, each complex comprising one of the multiple particles and at least one of the optical labels, and detecting complexes present within a subset of the mixture.

The mixture can comprise at least about 95% of the volume V of liquid sample.

The method can further comprise detecting complexes present within each of multiple different subsets of the mixture.

A total volume of the multiple different subsets can be at least 90% of a volume of the liquid sample introduced to the microfluidic device.

In another aspect, a device for detecting an analyte comprises: a cartridge having a microfluidic channel including an inlet and a detection region in fluid communication with the inlet; a microfluidic flow path having an at least partially deformable wall and in fluid communication with the detection region of the channel; and a cap having a sealing member configured to seal with the inlet and form a fluid circuit including the inlet, the microfluidic channel and the microfluidic flow path.

The cap and cartridge of the device can be configured to close irreversibly after forming the fluid circuit.

Alternatively, the cap can be flexibly attached to the cartridge.

Further, the cap and cartridge can be configured to engage in a first relative position such that the cap can be removed and to engage in a second relative position such that the cap is irreversibly closed after forming the fluid circuit.

The detection region can be bounded by at least one surface of the cartridge and at least one surface of a lid. The lid can include a transparent film over the detection region. Further, the lid can be adhesively affixed to the cartridge.

In another aspect, a device for detecting an analyte comprises a cartridge having a microfluidic channel including a capillary inlet having an anticoagulant on an inner surface, a chamber including a reagent, and a detection region in fluid communication with the inlet; a microfluidic flow path having an at least partially deformable wall and in fluid communication with the detection region of the channel; and a cap having a sealing member configured to seal with the inlet and form a fluid circuit including the inlet, the microfluidic channel and the microfluidic flow path.

In another aspect, a fluorescence detector includes a light source; a condenser lens obtaining a solid angle of 10° or greater; and an objective lens obtaining a solid angle of 10° or greater and being configured to image a microscopic object.

The condenser lens and/or the objective lens can obtain a solid angle of 10° to 15°, such as 12° to 14°, e.g. 13.5°.

The fluorescence detector can further include an aperture. The aperture can be configured to allow a solid angle of 10° or greater (e.g. 10° to 15°, or 12° to 14° or 13.5°).

The fluorescence detector can further include at least one filter. Filters can be chosen with regard to a predetermined set of emission wavelengths. E.g., one filter can be selected to pass light with one specific wavelength and another filter can be selected to pass light with a different specific wavelength, e.g. depending on the emission wavelengths of dyes used for labelling reagents in the cartridge.

In another aspect, a system for detecting an analyte comprises:

a cartridge having: a microfluidic channel including an inlet and a detection region in fluid communication with the inlet; a micro fluidic flow path having an at least partially deformable wall and in fluid communication with the detection region of the channel; and a cap having a sealing member configured to seal with the inlet and form a fluid circuit including the inlet, the microfluidic channel and the microfluidic flow path; and a fluorescence detector including a light source; a condenser lens obtaining a solid angle of 10° or greater; and an objective lens obtaining a solid angle of 10° or greater.

The fluorescence detector can include a camera.

Further, the fluorescence detector can include one or more selectable emission filters.

In another aspect, a method of detecting an analyte in a liquid sample comprises:

introducing the liquid sample into a microfluidic channel thereby forming a contiguous liquid slug enclosed by the channel and bounded at a first end by a transport fluid;

forming a fluid circuit such that the transport fluid provides fluid communication between the first and second ends of the liquid slug; and applying a differential pressure to the first and second ends of the liquid slug via the transport fluid.

In another aspect, a method of detecting an analyte in a liquid sample comprises:

introducing the liquid sample into a microfluidic channel thereby forming a contiguous liquid slug enclosed by the channel and bounded at a first end by a transport fluid, the liquid sample comprising multiple particles, forming a fluid circuit such that the transport fluid provides fluid communication between the first and second ends of the liquid slug, forming a mixture comprising at least a portion of the liquid sample and an optical label by applying a differential pressure to the first and second ends of the liquid slug via the transport fluid, forming multiple complexes, each complex comprising one of the multiple particles and at least one of the optical labels, and detecting complexes present within a subset of the mixture.

Next, further exemplary embodiments of the devices and methods (e.g., of the devices, systems and methods for detecting an analyte) will be explained.

A portion of the fluid circuit can be formed by an elastically deformable wall.

Applying a differential pressure to the first and second ends of the liquid slug can include compressing the elastically deformable wall.

The liquid sample can be selected as desired based on the analytes to be determined. Exemplary samples include water, aqueous solutions, organic solutions, inorganic solutions, bodily fluids of humans and other animals, for example, urine, sputum, saliva, cerebrospinal fluid, whole blood and blood-derived materials such as plasma and sera.

The analytes to be determined can be selected as desired. For example, the analytes can relate to medicine (e.g., diagnostics), research (e.g., drug discovery), industry (e.g. water or food quality monitoring), or forensics. Exemplary analytes to be determined include markers (e.g., diagnostic markers or predictive markers) of physiological conditions such as disease. Such markers include cardiac markers (e.g., natriuretic peptides and members of the troponin family), cancer markers (e.g., nuclear matrix proteins), genetic markers (e.g., polynucleotides), sepsis markers, neurological markers, and markers indicative of pathogenic conditions. The analytes can be indicative of the presence of pathogens (e.g., bacteria, viruses, or fungi).

In a typical embodiment, one or more of the analytes comprise particles such as viruses, bacteria, cells, fungi, or spores. For example, any of the particles described in International Patent Application PCT/EP2006/068153 (which is incorporated by reference in its entirety) can be detected. Examples of naturally occurring particles include inter alia prokaryotic cells (e.g. bacterial cells such as *Escherichia coli* or *Bacillus subtilis*), eukaryotic cells (e.g. yeast cells such as *Saccharomyces cerevisiae*, insect cells such as Sf9 or High 5 cells, immortalized cell lines such as HeLa or Cos cells, and primary cells such as mammalian blood cells) or viruses (e.g. phage particles such as M13 or T7 phage). In one embodiment, the particles can be cells.

The labels or probe compounds or capture molecules can be selected as desired based on the analytes to be determined. Suitable labels or probe compounds for determining the presence of an analyte are described in U.S. provisional application 60/826,678 filed Sep. 22, 2006, which is incorporated by reference in its entirety. A label or a capture molecule or a probe or a probe molecule or a molecular probe is understood to denote a molecule or a complex, which is used for the detection of other molecules due to a particular characteristic binding behavior or a particular reactivity. Exemplary probe compounds include biopolymers such as peptides, proteins, antigens, antibodies, carbohydrates, nucleic acids, and/or analogs thereof and/or mixed polymers of the above-mentioned biopolymers.

Detectable markers or labels that can be used according to the invention include any compound, which directly or indirectly generates a detectable compound or signal in a chemical, physical or enzymatic reaction. Preferably, the labels can be selected inter alia from enzyme labels, colored labels, fluorescent labels, chromogenic labels, luminescent labels, radioactive labels, haptens, biotin, metal complexes, metals, and colloidal gold, with fluorescent labels being particularly preferred. All these types of labels are well established in the art. An example of a physical reaction that is mediated by such labels is the emission of fluorescence. Hence, the optical labels can be fluorescent labels.

The methods can further comprise labeling the analyte with a first optical label and a second optical label antibody, wherein the first and second optical label are different. The first and second optical labels can be first and second fluorescent labels which have distinct emission wavelengths. The label can be an antibody. E.g., the method can further comprise labeling the analyte with a first optical label fluorescent antibody and a second fluorescent antibody, wherein the first and second fluorescent antibodies have distinct emission wavelengths.

Detecting the analyte can include recording a first image of the analyte at the emission wavelength of the first fluorescent antibody; recording a second image of the analyte at the emission wavelength of the second fluorescent antibody; and comparing the first and second images.

The methods can further comprise detecting complexes present within each of multiple different subsets of the mixture. E.g., within each mixture of the microfluidic device, particles, if present, can combine with detectable label to form complexes. After a suitable incubation period to permit complex formation, the presence of complexes is detected. Examples of detection of complexes is described in International Patent Application PCT/EP2006/068153, which is incorporated by reference in its entirety.

A total volume of the multiple different subsets can be at least 90% of a volume of the liquid sample introduced to the microfluidic device.

The methods can further comprise introducing a total volume V of liquid sample to the microfluidic device wherein a total volume of the mixture can be at least about 90% or at least about 95% of the volume V.

The methods can further comprise detecting complexes present within at least 10% of the total volume of the mixture, e.g. within 10% to 90%, 15% to 50% or 20% to 30% of the total volume of the mixture.

The microfluidic channel can include an inlet and a detection region in fluid communication with the inlet. Further, the microfluidic channel can be a microfluidic channel of a microfluidic device.

The methods can further comprise, prior to introducing a liquid sample into a microfluidic channel, introducing a liquid sample to a bore of a capillary.

The capillary is typically a standard capillary (e.g., an end-to-end capillary such as a plastic capillary). An end-to-end capillary includes an internal bore and first and second openings, one at either end of the bore. The capillary bore can comprise a coagulation inhibitor such as heparin. E.g., the capillary can be anti-coagulant coated such as with heparin. In general, the capillary bore is configured to contain a total volume V of liquid sample. Volume V is typically about 25 microliters or less (e.g., about 20 microliters or less, about 15 microliters or less, about 10 microliters or less, about 5 microliters or less). In general, volume V is about 1 microliters or more (e.g., about 3 or 5 or 7.5 microliters or more).

The methods can further comprise, intermediate the steps of introducing the liquid sample to the bore of the capillary and introducing the liquid sample into the microfluidic channel, connecting the capillary to the microfluidic device, the liquid sample remaining within the capillary.

The methods can further comprise optically detecting a signal indicative of an amount of complex present within a subset of the liquid sample, the subset being present within a detection zone or detection region of the microfluidic device.

In some embodiments, the exit of the capillary opens out to a reaction chamber with a predetermined volume of, e.g., about 5 μL, 10 μL or 20 μL. In some embodiments, the reaction chamber includes a reagent pellet. The reagent pellet can include labels, e.g. antibodies labelled with a fluorescent dye and having an affinity for antigens to be detected within the sample. For instance, for detecting the number of T-helper-cells in a liquid sample the reagent pellet can include an anti-CD4+-antibody labelled with a first fluorescent dye (such as phycoerythrine) and an anti-CD3+-antibody labelled with a second fluorescent dye such as (phycoerythrine-Cy5), salts and stabilizing reagents etc. In some embodiments, the inner surface of the first zone is covered with reagents necessary for processing the sample. An exemplary assay for detecting particles such as cells in a liquid sample is described in, for example, in WO 2007/051861, which is incorporated by reference in its entirety. As described in WO 2007/051861, detection can take place in the microfluidic channel. Thus, the microfluidic channel is at least partially optically transparent. For example, the microfluidic channel can be covered by an at least partially optically transmissible layer.

Introducing the liquid sample can be performed by compressing the elastically deformable wall. Compressing the elastically deformable wall can comprise compressing a first portion of the fluid circuit and, without first completely releasing the compression, moving a site of the compression along the fluid circuit by an amount sufficient to perform the steps of displacing and introducing.

The methods can further comprise performing the step of optically detecting a signal indicative of an amount of complex present within the different subset with first completely releasing the compression.

The methods can further comprise intermediate the steps of introducing the liquid sample to the bore of the capillary and introducing at least the portion of the liquid sample into the microfluidic channel, stopping the liquid sample from exiting the capillary.

In some embodiments, a detection region of the microfluidic channel does not support capillary flow of the liquid sample.

Further, at least a part of an interior surface of the microfluidic channel can be hydrophobic.

The methods can further comprise moving at least one of the microfluidic device and an optical detector with respect to one another and subsequently detecting an optical signal indicative of an amount of complex present within a different subset of the liquid sample.

BRIEF DESCRIPTION OF THE DRAWINGS

FIG. 5 is only a partial side view.

DETAILED DESCRIPTION

Figure 1:
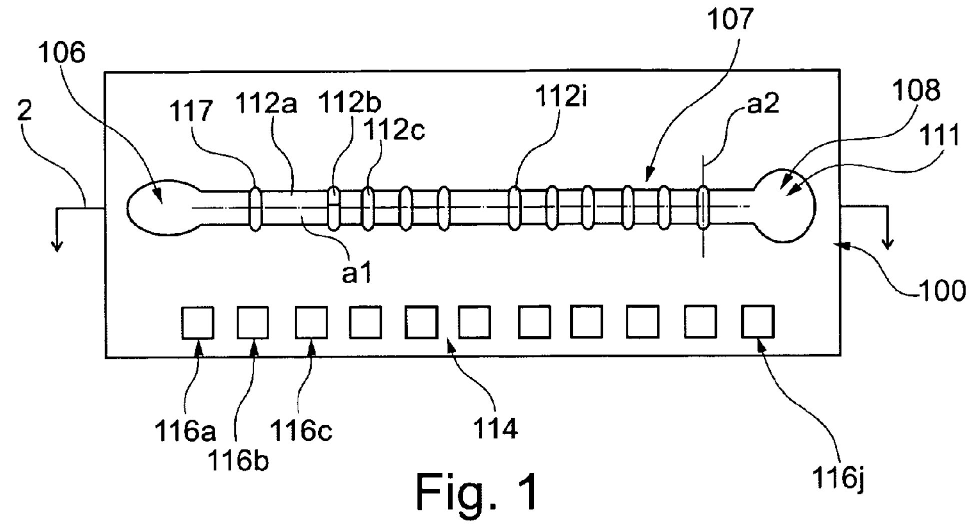
FIG. 1 illustrates a microfluidic device.

A method for assaying a sample to determine the presence (e.g., qualitatively and/or quantitatively) of multiple analytes includes introducing the sample into a channel of a microfluidic device. The microfluidic device can have a single channel or multiple channels, depending on the design and complexity of the assay. In some embodiments, the channel can be defined between opposed inner surfaces of first and second substrates of the device.

In general, a device for performing assays can include a microfluidic flow path that is bounded by at least one deformable surface. For example, where the microfluidic flow path is defined be between opposed inner surfaces of first and second substrates of the device the second substrate can be relatively flexible compared to the first substrate. In another example, a portion of the microfluidic flow path can include a compressible zone. The compressible zone can be a length of the fluid circuit along which at least one wall of the circuit is compressible or deformable. When a localized compressive force is applied to the deformable surface, the surface deforms. Under a sufficient force, the deformable surface can be compressed to a degree that interrupts the microfluidic flow path. Moving the location of the surface deformation relative to the microfluidic flow path can move liquid within the microfluidic flow path, particularly when the deformable surface is compressed to a degree that interrupts the microfluidic flow path.

In some embodiments, the second substrate can be relatively flexible compared to the first substrate. Multiple test zones can be spaced apart along the channel. Each test zone includes an immobilized probe compound configured to participate in an assay for a respective analyte. Typically, each assay includes interaction of a probe compound with the respective analyte or with a respective complex including the analyte and a reagent (e.g., an optical label).

To determine the assay result for each test zone, the outer surface of the second substrate can be subjected to a localized compressive force. The compressive force causes a localized reduction of the distance separating the inner surfaces of the first and second substrates. The location of the localized distance reduction overlaps an optical detection zone defined within the channel. As the distance is reduced, mobile material (e.g., sample, unbound optical probes, and/or reagents) is displaced from between the substrates at the detection zone. The microfluidic device is translated so that the test zones pass sequentially through the detection zone. For each test zone, the assay result is optically determined (e.g., by fluorescence) as the test zone passes through the detection zone. The presence of each analyte is determined (e.g., quantitatively and/or qualitatively) based on the assay result.

The assay results can typically determined without first contacting the test zones with a wash solution after contacting the test zones with the sample.

The analytes to be determined can be selected as desired. For example, the analytes can relate to medicine (e.g., diagnostics), research (e.g., drug discovery), industry (e.g. water or food quality monitoring), or forensics. Exemplary analytes to be determined include markers (e.g., diagnostic markers or predictive markers) of physiological conditions such as disease. Such markers include cardiac markers (e.g., natriuretic peptides and members of the troponin family), cancer markers (e.g., nuclear matrix proteins), genetic markers (e.g., polynucleotides), sepsis markers, neurological markers, and markers indicative of pathogenic conditions. The analytes can be indicative of the presence of pathogens (e.g., bacteria, viruses, or fungi).

The probe compounds of the test zones can be selected as desired based on the analytes to be determined. Exemplary probe compounds include polynucleotides, antibodies, and proteins.

The sample liquid can be selected as desired based on the analytes to be determined. Exemplary samples include water, aqueous solutions, organic solutions, inorganic solutions, bodily fluids of humans and other animals, for example, urine, sputum, saliva, cerebrospinal fluid, whole blood and blood-derived materials such as plasma and sera.

Figure 2:
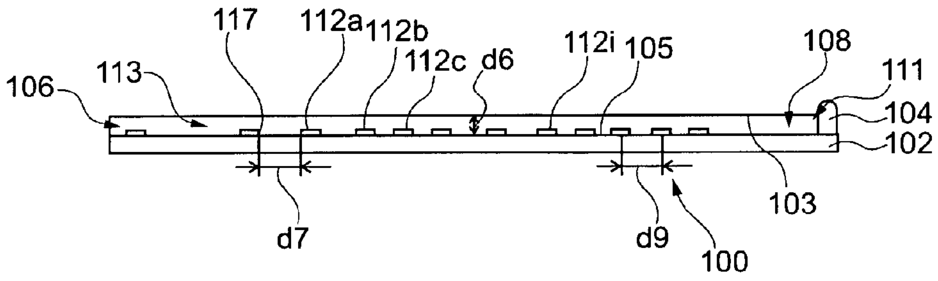
FIG. 2 is a side view of the microfluidic device of FIG. 1.
Figure 4:
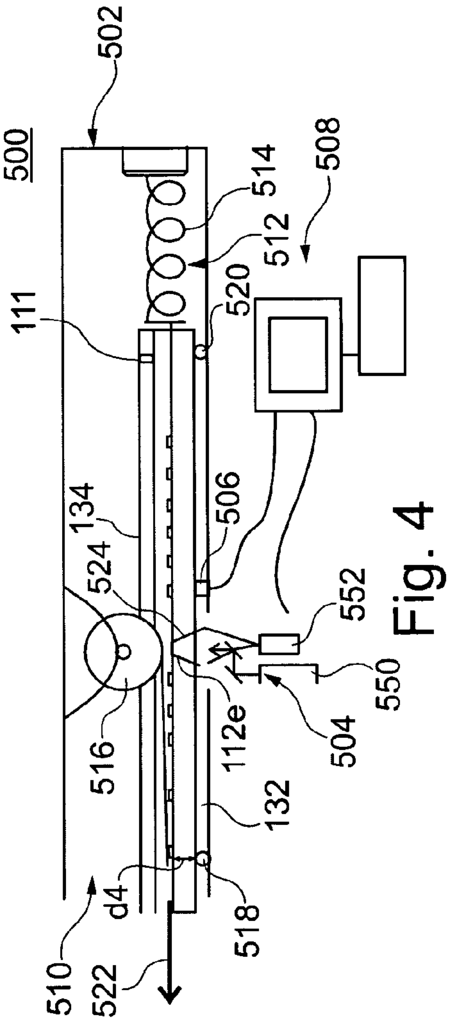
FIGS. 4 and 5 are side views of a system configured to operate the microfluidic device of FIG. 1.

Referring to FIGS. 1, 2, and 4 a microfluidic device 100 and an operating system 500 can be used to assay a sample to determine the presence (e.g., qualitatively and/or quantitatively) of multiple analytes. Microfluidic device 100 includes first and second substrates 102,104 defining a microfluidic network 107 including an inlet 106 and, in communication therewith, a channel 110 and a reservoir 108. Multiple spaced apart test zones 112*i* are disposed within channel 110. Each test zone 112*i* includes one or more reagents (e.g., probe compounds) configured to participate in an assay for an analyte. Channel 110 also includes a reference zone 117. Device 100 also includes a reference pattern 114 including multiple indicia 116*j*. Reference pattern 114 provides information related to spatial properties of test zones 112*i*.

Operating system 500 includes a housing 502, a detector 504, a reference pattern reader 506, and a processor in communication with detector 504 and pattern reader 508. Detector 504 is an optical fluorescence detector that detects interaction between a sample and test zones 112*i*. Detector 504 includes a light source 550 (e.g., a light emitting diode or a laser diode) and a zero$^{th}$ order light sensitive detector 552 (e.g., a photomultiplier tube or a photodiode, such as an avalanche photodiode). Reference pattern reader 506 reads reference pattern 114 of device 100 during operation of system 500.

We now discuss microfluidic device 100 and system 500 in greater detail.

First substrate 102 is typically optically transmissive (e.g., clear) with respect to a wavelength of light useful for exciting and detecting fluorescence from fluorescent labels. For example, first substrate 102 may transmit at least about 75% (e.g., at least about 85%, at least about 90%) of incident light in a least one wavelength range between about 350 nm and about 800 nm. First substrate 102 can be formed of, for example, a polymer, glass, or silica. Second substrate 104 is typically formed of a pliable or flexible material (e.g., an elastomeric polymer). First substrate 102 may be less flexible than second substrate 104. For example, first substrate 102 may be substantially rigid (e.g., sufficiently rigid to facilitate handling of device 100).

Channel 110 is a capillary channel. A sample 113 applied to inlet 106 migrates along channel 110 by capillary force. Channel 110 is oriented along a major axis a1. Reservoir 108 includes a vent 111 to prevent gas buildup ahead of the sample.

Each test zone 112*i* typically includes a reagent (e.g., a probe compound) configured to provide a detectable interaction in the presence of an analyte. The interaction can include, for example, binding of a corresponding analyte to a probe compound of the test site and/or a chemical reaction between the corresponding analyte and the probe compound. The reaction results in a detectable product (e.g., a precipitate). Exemplary probe compounds include proteins, antibodies, and polynucleotides. Suitable probe compounds for determining the presence of an analyte are described in U.S. provisional application 60/826,678 filed Sep. 22, 2006, which is incorporated by reference in its entirety.

Figure 3A:
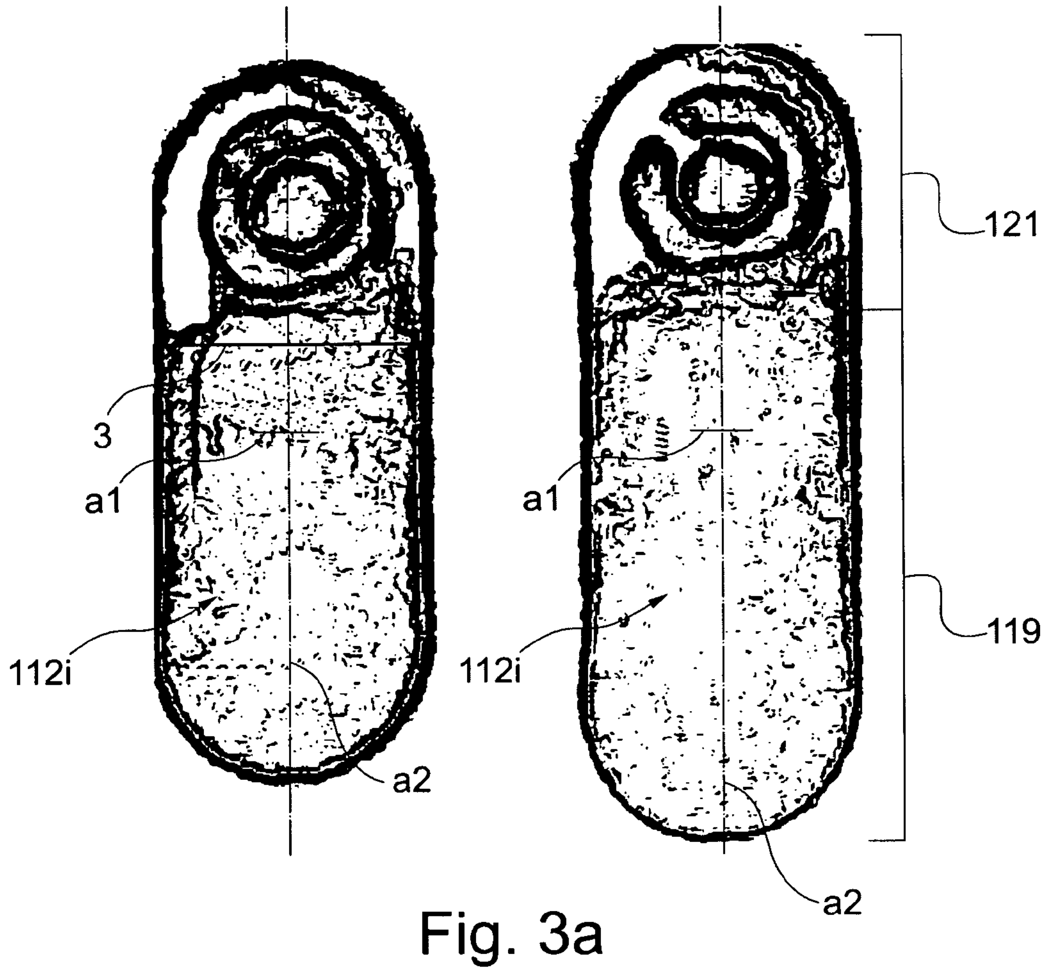
FIG. 3*a* shows top views of two test zones of the microfluidic device of FIG. 1.

Referring also to FIG. 3*a*, each test zone 112*i* is elongate having a major axis a2 oriented generally perpendicular to major axis a1 of channel 110. Typically, a ratio of a length along major axis a2 to a width w along a perpendicular dimension of the test zones 112 is at least 2.5 (e.g., at least 5). The length along axis a2 is typically at least about 200 μm (e.g., at least about 350 microns) and typically about 2000 μm or less (e.g., about 1000 μm or less, about 750 μm or less). Width w is typically at least about 25 μm (e.g., at least about 50 microns) and typically about 500 μm or less (e.g., about 250 μm or less, about 150 μm or less). In an exemplary embodiment, test zones 112 are about 500 μm long and about 100 μm wide.

As seen in FIG. 2, test zones 112*i* are spaced apart from adjacent test zones by a distance d7 along channel 110. Distance d7 between test zones 112*i* is discussed further below in relation to a detection zone of detector 504.

Test zones 112*i* can be formed as desired. In general, the reagents are contacted with the first substrate. Then, the reagents and substrate are relatively translated laterally to form an elongated test zone.

Figures 3B, 3C, 3D, 3E, 3F, 3G:
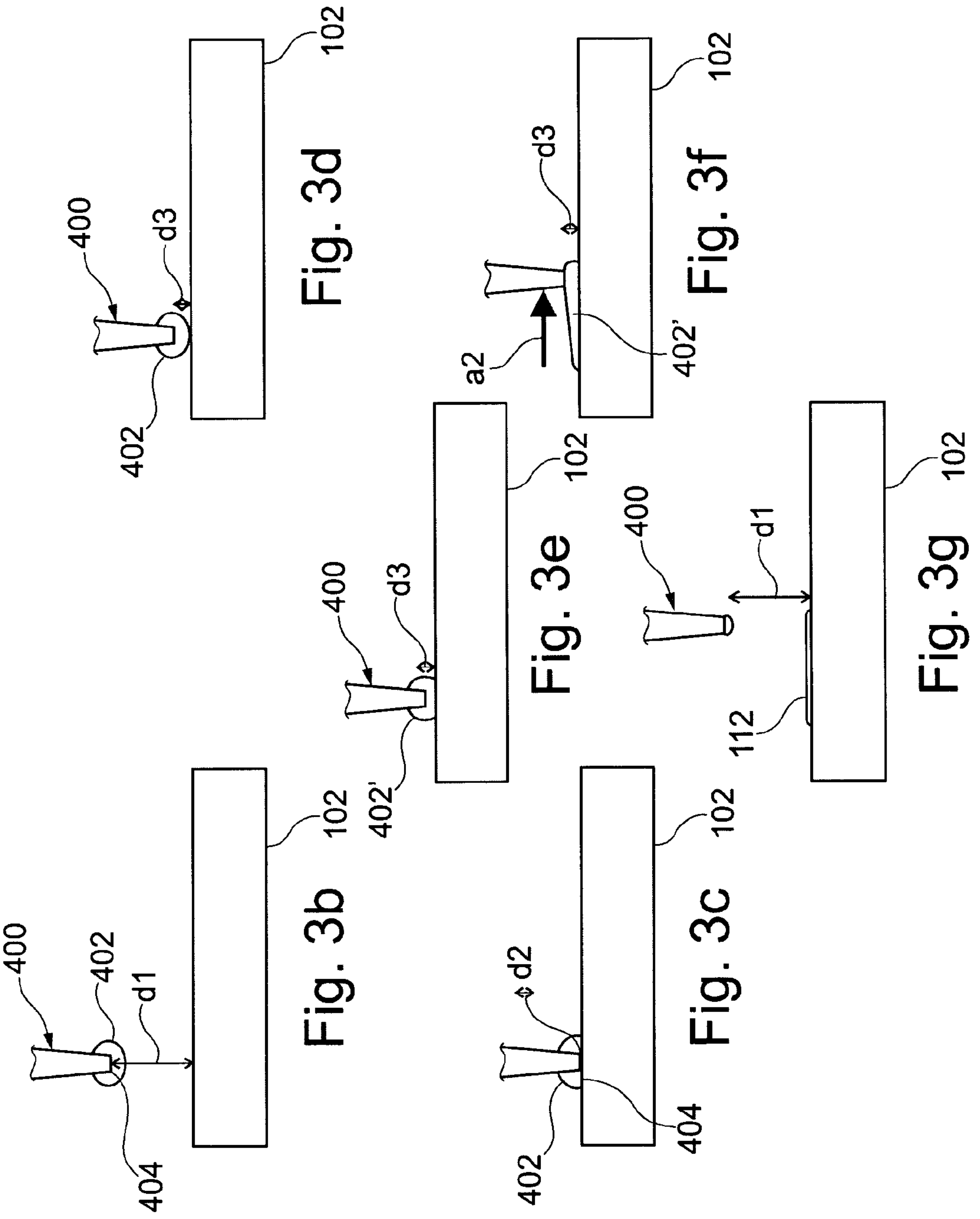
FIGS. 3*b* to 3*g* illustrate a method for forming the test zone of FIG. 3*a*.

Referring to FIGS. 3*b*-3*g*, a method for forming test zones 112*i* includes dispensing reagents from a capillary spotter 400 onto first substrate 102. In FIG. 3*b*, an amount (e.g., between about 2 and 8 nl, between about 3 and 5 nl) of reagent solution 402 containing one or more probe compounds is introduced to a distal tip 404 of a capillary of a capillary spotter. Distal tip 404 typically has a diameter of between about 80 and 120 μm (e.g., about 100 μm). Reagent solution 402 and substrate 102 are initially separated (e.g., not in contact) by a distance d1. Typically, d1 is at least about 250 μm (e.g., about 500 μm).

In FIG. 3*c*, tip 404 and substrate 102 are brought to a smaller separation d2 so that reagent solution 402 contacts a location of substrate 102. At the smaller separation d2, distal tip 404 is adjacent the location of substrate 102 (e.g., touching so that d2 is zero). Distal tip 404 and substrate 102 are maintained for a time (e.g., about 1 second or less, about 0.5 seconds or less, about 0.25 second or less) at separation d2 in the adjacent (e.g., touching) position. In some embodiments, the time for which distal tip 402 is maintained in the adjacent (e.g., touching) position is indistinguishable from zero.

In FIG. 3*d*, distal tip 404 and substrate 102 are moved to an intermediate separation d3 in which distal tip 404 and substrate remain connected by reagent solution 402 of distal tip 404. Typically, intermediate separation d3 is at least about 5 μm (e.g., at least about 10 μm) and about 30 μm or less, about 25 μm or less). In an exemplary embodiment, intermediate separation d3 is about 20 μm.

In FIG. 3*e*, distal tip 404 and substrate 102 are maintained at intermediate separation d3 for an incubation time so that at least some (e.g., at least about 10%, at least about 25%, at least about 40%) of reagent solution 402 at the distal tip evaporates so that only a remaining portion 402' of reagent solution 402 remains. Typically, only about 75% or less (e.g., about 50% or less) of reagent solution 402 evaporates to leave solution 402' remaining. The incubation time depends on the nature of the solution 402 (e.g., the probe compound concentration and the solvent vapor pressure) and distal tip 404 environment (e.g., the relative humidity and temperature). Typical incubation times are longer (e.g., at least 5 times as long, at least 10 times as long, at least 20 times as long, at least about 35 times as long) than the period of time for which the tip and substrate are in the adjacent position d2. Exemplary incubation times are least about 5 seconds (e.g., at least about 10 seconds at least about 20 seconds, at least about 25 seconds).

In FIG. 3*f*, after the incubation time at intermediate separation d3, at least one of the distal tip 404 and substrate 102 are moved laterally relative to the other to dispense reagent solution 402' along a major axis a2. In FIG. 3*g*, at the completion of the lateral movement, distal tip 402 and substrate 102 are separated so that they are no longer connected by the reagent solution. For example, distal tip 404 and substrate 102 can be returned to initial separation d1. The method can be repeated (e.g., using different reagent solution) to dispense elongate test zones at each of multiple locations of the substrate.

In general, the vertical separation of the distal tip and substrate is changed by moving the distal tip relative to the substrate. In general, the lateral translation of the distal tip and substrate is performed by translating the substrate relative to the distal tip. Exemplary reagent solutions, probe compounds, and dispensing devices are described in U.S. provisional application 60/826,678 filed Sep. 22, 2006, which is incorporated by reference in its entirety.

Figure 8A:
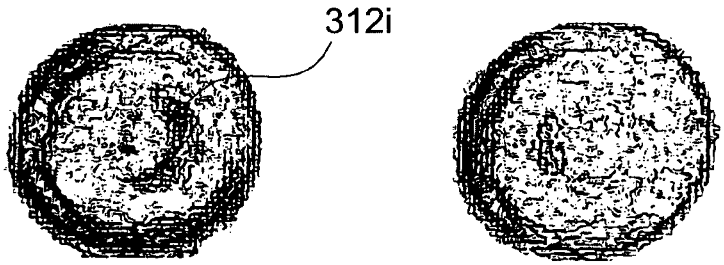
FIGS. 8*a* and 8*b* are each top views of two test zones of the microfluidic device of FIG. 7.
Figure 8B:
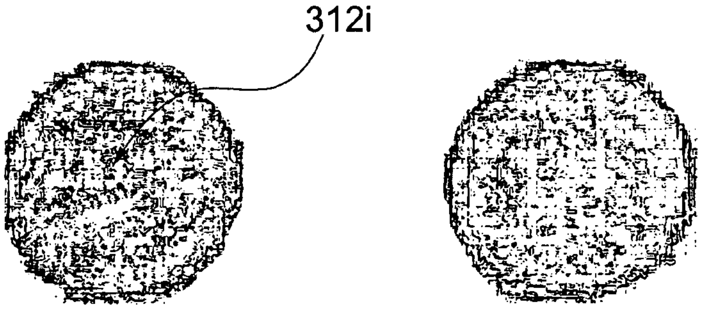

As seen in FIG. 3*a* and referring also to FIGS. 8*a* and 8*b*, the method for producing elongate test zones 112*i* provides a more homogenous distribution of probe compounds than a dispensing method that omits the step of lateral moving the distal tip and substrate. Test zones 112*i* include a first portion 119 and a second portion 121. The distribution of probe compounds in the first portion 119 is more homogenous than in second portion 121 or in test zones 312*i*, which were prepared without the step of lateral movement.

Returning to FIG. 1, reference zone 117 produces a response detectable by detector 504 independent of the presence of any analyte in a sample. Reference zone 117 typically includes a fluorescent medium (e.g., a polymer or immobilized fluorescent molecule). Reference zone 117 is discussed further below in regard to operation of system 500.

Indicia 116*j* of reference pattern 114 are configured to be read by reference pattern reader 506 of system 500. Indicia 116*j* are composed of magnetic material (e.g., magnetic ink). Pattern reader 506 can detect the presence of indicia 116*j*. Reference pattern 114 is discussed further below in regard to operation of system 500.

Returning to FIG. 4, housing 502 of operating system 500 includes an opening 510 to receive device 100, a compression system including a compression roller 516 and support rollers 518,520, and a translation actuator 512 including a damped spring 514. When device 100 is received within housing 500, detector 504 defines an optical detection zone 524 within channel 110. In use, device 100 is translated with respect to detection zone 524. Test zones 112*i* sequentially pass into and out of the detection zone. Detector 504 sequentially detects the interaction between a sample and successive test zones 112*i*. Detector 504 also senses reference zone 117.

Figure 6:
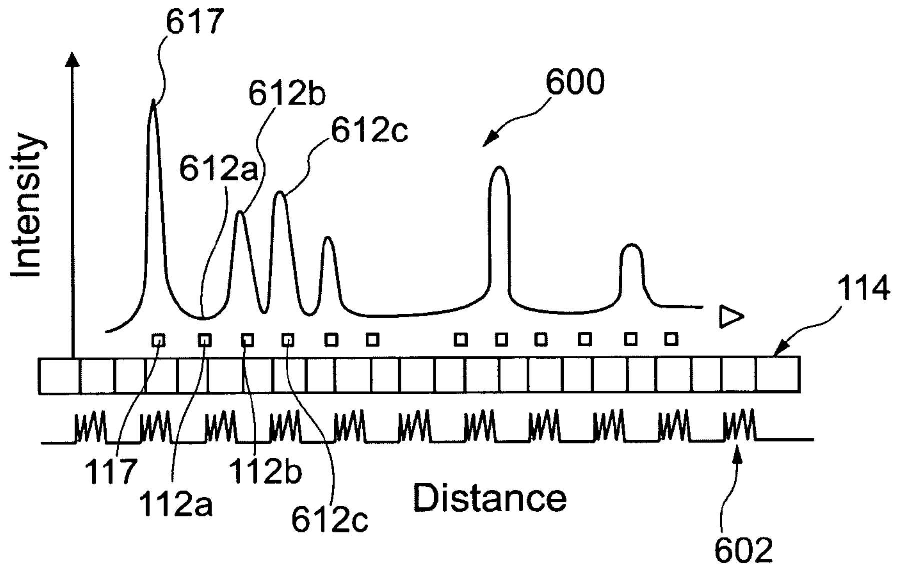
FIG. 6 illustrates fluorescence intensity data as a function of position along a channel of the microfluidic device of FIG. 1.

Referring to FIG. 6, detector 504 outputs a signal 600 as a function of the distance (relative or absolute) that device 100 is translated. Signal 600 includes a peak 617 indicative of reference zone 117 and peaks 612*i* indicative of the interaction at each zone 112*i*. Simultaneously, pattern reader 506 outputs a signal 602 indicative of indicia 116*i* as a function of distance that device 100 is translated. Because indicia 116*i* are related spatially to test zones 112*i*, processor 508 can determine when detection zone 524 coincides with a particular test zone even if that test zone exhibits no signal (e.g., as for test zone 112*a* which exhibits a signal 612*a* that is indistinguishable from zero). Reference zone 117 and corresponding signal 617 can be used alternatively or in combination with signal 602 to determine which regions of signal 600 correspond to particular test zones.

We next discuss the compression system. In use, the compression system compresses device 100 to reduce the distance between substrates 102,104 within channel 110. When device 100 is received within housing 502, an outer surface 132 of first substrate 102 is oriented toward support rollers 518,520 and an outer surface 134 of second substrate 104 is oriented toward compression roller 516. A distance d4 between support rollers 518,520 and compression roller 516 is less than a thickness t1 (FIG. 5) of device 100. Because second substrate 104 relatively flexible as compared to first substrate 102, compression roller 516 compresses second substrate 104 causing a local reduction in distance d6 between inner surface 103 of second substrate 104 and inner surface 105 of first substrate 102.

In the relaxed state (e.g., uncompressed state) (FIG. 2), distance d6 is typically at least about 25 μm (e.g., at least about 50 μm, at least about 75 μm). In the uncompressed state, distance d6 is typically about 500 μm or less (e.g., about 250 μm or less). In the locally reduced distance state (e.g., locally compressed state) (test zone 112*e* in FIG. 4), distance d6 is typically about 15 μm or less (e.g., about 10 μm or less, about 5 μm or less, e.g., about 2.5 μm or less). Examples of fluorescence detection performed between surfaces separated by a reduced distance state are described in U.S. continuation of International Patent Application PCT/EP2005/004923, which is incorporated by reference in its entirety.

Figure 5:
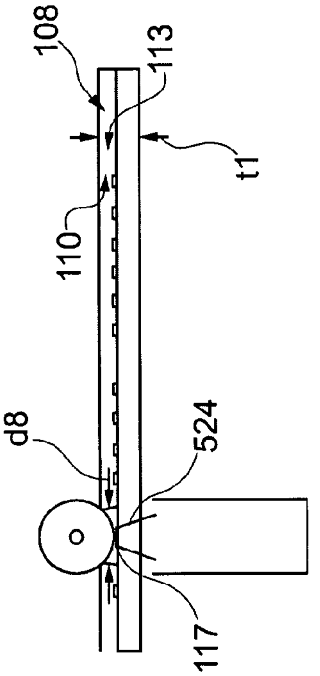

As seen in FIGS. 4 and 5, the compression system reduced distance d8 within channel 110 over only a portion of the length of channel 110. Typically, distance d8 is about 5 times the length or less (e.g., about 3 times the length or less, about 2 times the length or less, about the same as) than distance d7 separating test zones 112*i*.

Typically, distance d7 is large enough that optical detection zone 524 defined by detector 504 encompasses fewer than all (e.g., 5 or fewer, 3 or fewer, 2 or fewer) of test zones 112*i* within channel 110. In an exemplary embodiment, d7 is large enough that a width of detection zone 524 along major axis a1 of channel 110 does not simultaneously contact more than 3 (e.g., not more than two, not more than one) test zone 112*i*. A width of detection zone 524 perpendicular to major axis a1 of channel 110 is typically about the same as or less (e.g., no more than 75% of, no more than 50% percent of, no more than 30% of) the length of test zones 112*i* along axis a2 thereof.

In use, sample liquid is applied to inlet 106. Capillary force draws the sample along channel 110 toward reservoir 108. The sample liquid contacts test zones 112*i* along channel 110. Analytes within the sample interact with probe compounds of the test zones. After a suitable incubation time, device 100 is inserted into housing 500 to compress spring 514 of translation actuator 512. During insertion of device 100, compression roller 516 and support rollers 520 are spaced apart so that device 100 is not compressed. Once device 100 is fully inserted, detection zone 524 is positioned approximately overlapping reference zone 117. Compression roller 516 locally compresses channel 110 (FIG. 5).

When the interactions between the analytes of the sample and the test zones 112*i* are ready to be determined (e.g., after an incubation period), translation actuator 512 translates device 100 with respect to detection zone 524 of detector 504 (FIG. 4). Test zones 112*i* pass sequentially through detection zone 524 and are illuminated with light from light source. Compression roller 516 is arranged so that the localized reduction of distance d6 corresponds spatially to detection zone 524. Accordingly, light detector sequentially detects light from test zones 112*i* while each is in the locally reduced distance state (e.g., locally compressed state) (test zone 112*e* in FIG. 4). Fluorescence arising from each test zone is collected by lens and detected by light detector. The sequential localized reduction of distance d6 and optical determination continues until each test zone has translated through detection zone 524.

In addition to the probe compounds of each test zone and analytes, other materials are present in channel 110 between inner surface 103 of second substrate 104 and inner surface 105 of first substrate 102. Examples of such materials include sample concomitants and reagents (e.g., unbound or un-reacted optical probes). These materials typically produce background emission (e.g., fluorescence or scattered light) that is not associated with the interaction of the sample with test zones 112*i*. The intensity of the background emission is generally proportional to the amount of such materials remaining between the inner surfaces at the location corresponding to detection zone 524. The intensity of the optical signal that is indicative of the interaction at each test zone, however, is spatially localized in the vicinity of that test zone. Light detector receives and detects both fluorescence indicative of the interaction and the background emission.

Figure 9:
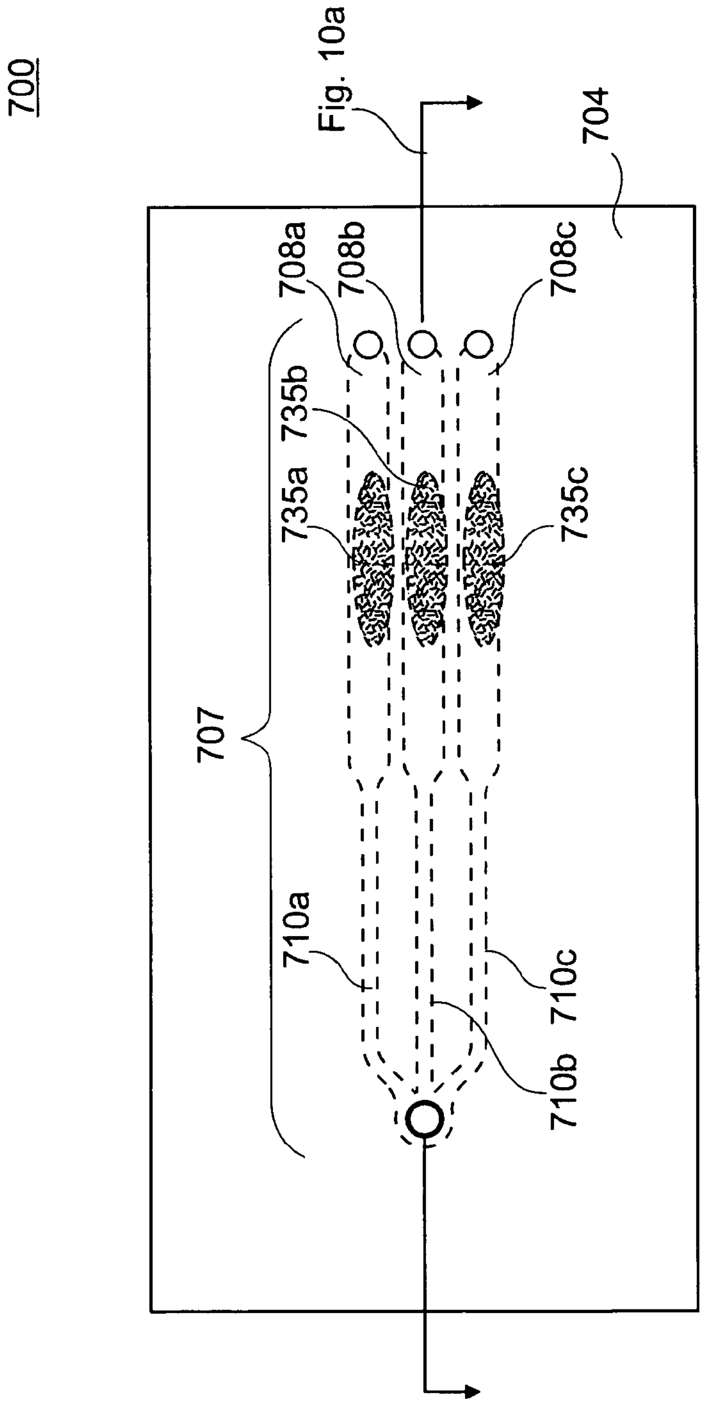
FIG. 9 illustrates a microfluidic device.
Figure 10A:
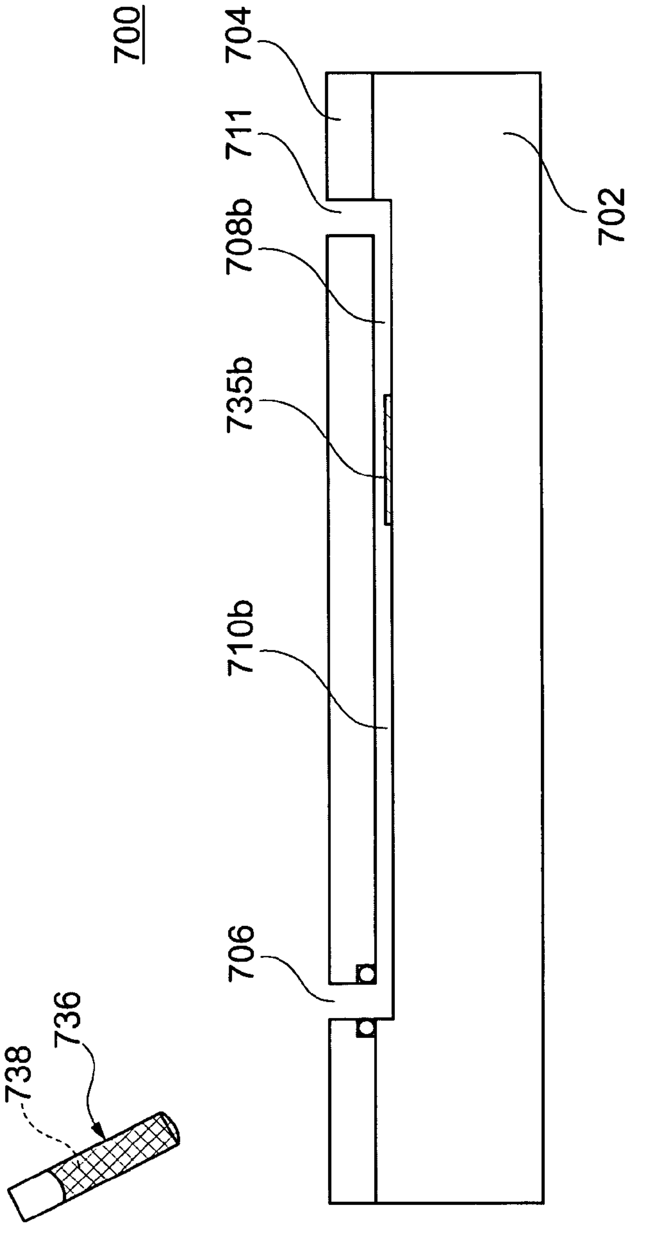
FIG. 10*a* is a cross-sectional side view of the microfluidic device of FIG. 9 and also illustrates a capillary tube containing liquid sample material.
Figure 11:
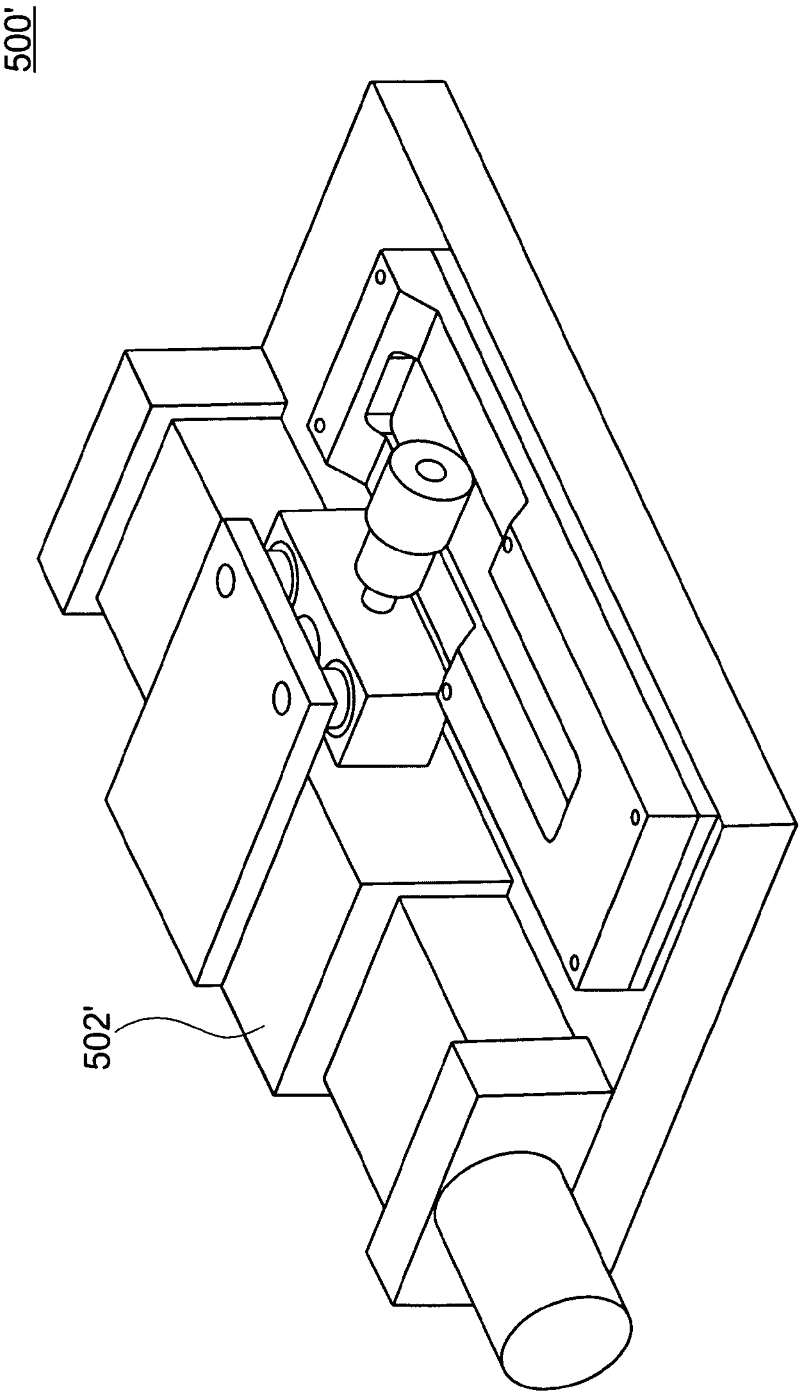
FIG. 11 illustrates an operating system for operating the microfluidic device of any of FIGS. 1, 7, and 9. The operating system can include any or all of the features of the operating system of FIGS. 4 and 5.

Referring to FIGS. 9, 10*a*, and 11, a microfluidic device 700 and an operating system 500' can be used to assay a sample to determine the presence (e.g., qualitatively and/or quantitatively) of one or more analytes. In a typical embodiment, one or more of the analytes comprise particles such as viruses, bacteria, cells, fungi, or spores. For example, any of the particles described in International Patent Application PCT/EP2006/068153 (which is incorporated by reference in its entirety) can be detected.

Microfluidic device 700 includes first and second substrates 702,704 defining a microfluidic network 707 including an inlet 706 and, in communication therewith, multiple channels 710*a*,710*b*,710*c* each having a respective reservoir 708*a*,708*b*,708*c*. Each reservoir includes a reagent material 709*a*,709*b*,709*c* (e.g., a probe compound) configured to participate in an assay for an analyte. Device 700 may include a reference pattern 114 including multiple indicia 116*j* (not shown in FIGS. 9, 10*a*, 11) which may be the same as that discussed above.

Operating system 500' includes a housing 502', a detector 504', a reference pattern reader (not shown), and a processor in communication with detector 504' and pattern reader. Detector 504 is an optical fluorescence detector that detects complexes comprising an analyte (e.g., a particle) and a detectable label (e.g., an optical label). Examples of suitable labels are described in International Patent Application PCT/EP2006/068153, which is incorporated by reference in its entirety. Detector 504' includes a light source 550' (e.g., a light emitting diode or a laser diode) and an optical detector 552' (e.g., a first order detector such as a diode array or a multidimensional detector (e.g., an imaging detector such as a charge coupled detector)). The optical detector typically and spatially selectively detects light from a respective detection zone defined within each channel of the microfluidic device.

We now discuss microfluidic device 700 and system 500' in greater detail.

First substrate 702 is typically optically transmissive (e.g., clear) with respect to a wavelength of light useful for exciting and detecting fluorescence from fluorescent labels. For example, first substrate 702 may transmit at least about 75% (e.g., at least about 85%, at least about 90%) of incident light in a least one wavelength range between about 350 nm and about 800 nm. First substrate 702 can be formed of, for example, a polymer, glass, or silica. Second substrate 704 is typically formed of a pliable or flexible material (e.g., an elastomeric polymer). First substrate 702 may be less flexible than second substrate 704. For example, first substrate 702 may be substantially rigid (e.g., sufficiently rigid to facilitate handling of device 700).

Channels 710*a*-710*c* typically support movement of liquid sample therein but are typically not capillary channels (i.e., liquid typically does not move within the channels of device 700 by capillary action). For example, one or more internal surfaces of the channels may be hydrophobic to inhibit capillary movement of the liquid sample. Alternatively, or in combination, the internal dimensions of the channels may be too large to permit capillary forces to drive substantial movement of the sample therein. Of course, in some embodiments, the channels may be capillary channels.

Device 700 is shown with 3 channels and corresponding reservoir but generally has a number N channels and corresponding reservoirs where N is at least 1 and is typically less than 20.

Each reservoir 708*i* typically includes a reagent 735*i* (e.g., a detectable label such as an optical label) configured to provide a detectable interaction in the presence of an analyte. The interaction can include, for example, binding of a corresponding analyte to a label to form complex comprising the analyte and one or more of the labels. Examples of such complexes are described in International Patent Application PCT/EP2006/068153 (which is incorporated by reference in its entirety). Each reagent is typically configured to permit detection of a different analyte.

Referring to FIGS. 10*b*-10*f*, device 700 can be operated as follows. An amount of liquid sample 738 (e.g., a biological liquid such as blood, saliva, or urine) is introduced to a capillary 736. Capillary 737 is typically a standard capillary (e.g., an end-to-end capillary such as a plastic capillary). An end-to-end capillary includes an internal bore and first and second openings, one at either end of the bore. The capillary may be anti-coagulant coated such as with heparin. Examples of suitable capillaries include 20 μl heparin coated capillaries available from Kabe Labortechnik (Nürnbrecht-Elsenroth, Deutschland; http://www.kabe-labortechnik.de/index.php?sprache=de&akt_seite=startseite_produkte.php). In general, the capillary bore is configured to contain a total volume V of liquid sample. Volume V is typically about 25 microliters or less (e.g., about 20 microliters or less, about 15 microliters or less, about 10 microliters or less). In general, volume V is about 5 microliters or more (e.g., about 7.5 microliters or more).

Figure 10B:
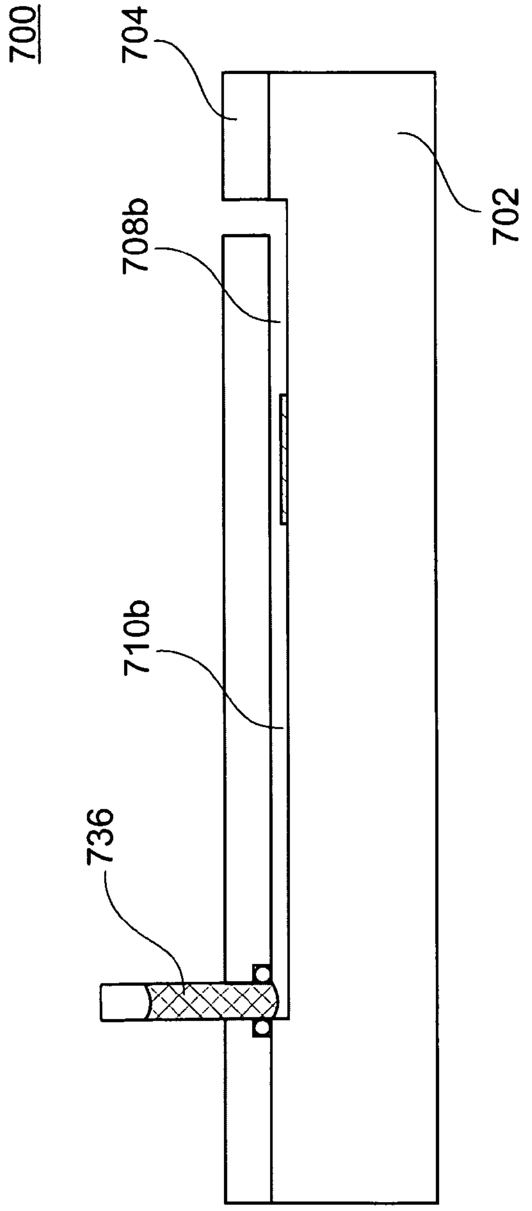
FIG. 10*b* illustrates the microfluidic device of FIG. 10*a* with the capillary tube having been connected with an inlet of the microfluidic device, the liquid sample not having entered a microfluidic network of the microfluidic device.

As seen in FIG. 10*b*, inlet 706 of device 700 is configured to accommodate capillary 736. Sample 737 typically remains within capillary 736 and does not enter the microfluidic device until subjected to an introduction force.

Figure 10C:
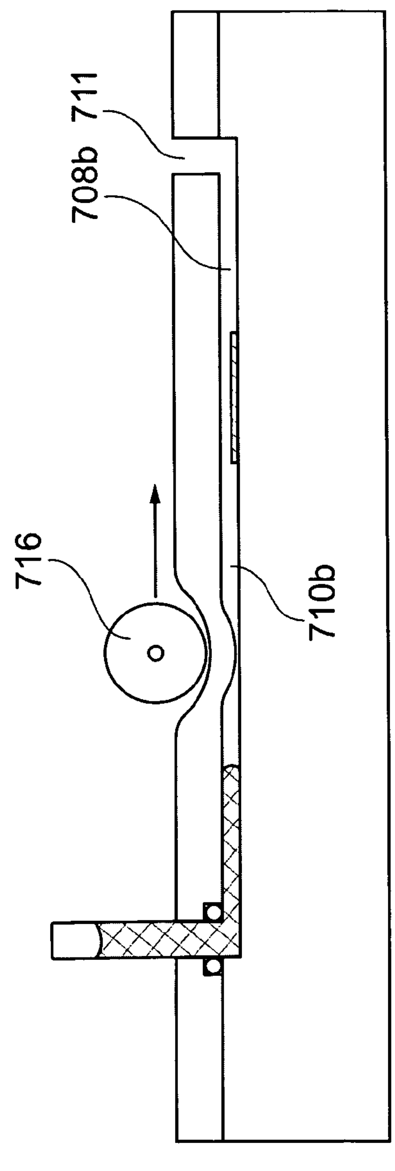
FIG. 10*c* illustrates the microfluidic device of FIG. 10*c* with a portion of the liquid sample having been drawn from the sample capillary into the microfluidic network of the microfluidic device.

As seen in FIG. 10*c*, an introduction force can be applied to sample 737 by reducing a distance between internal surfaces of substrates 702,704 to reduce a volume within the microfluidic network. For example, FIG. 10*c* illustrates a roller moving along an a portion of the microfluidic network. Typically, the compression causes the opposed internal surfaces to contact one another. As the volume within the channel increases following decompression of a given region of channel, a reduction in the gas pressure acting upon an internal surface 739 of the liquid sample 737 causes the sample to be forced into the microfluidic network. The compression and decompression can be performed in a single continuous movement of roller 716 along the microfluidic network or can be performed sequentially in multiple steps as in a peristaltic fashion.

Figure 10D:
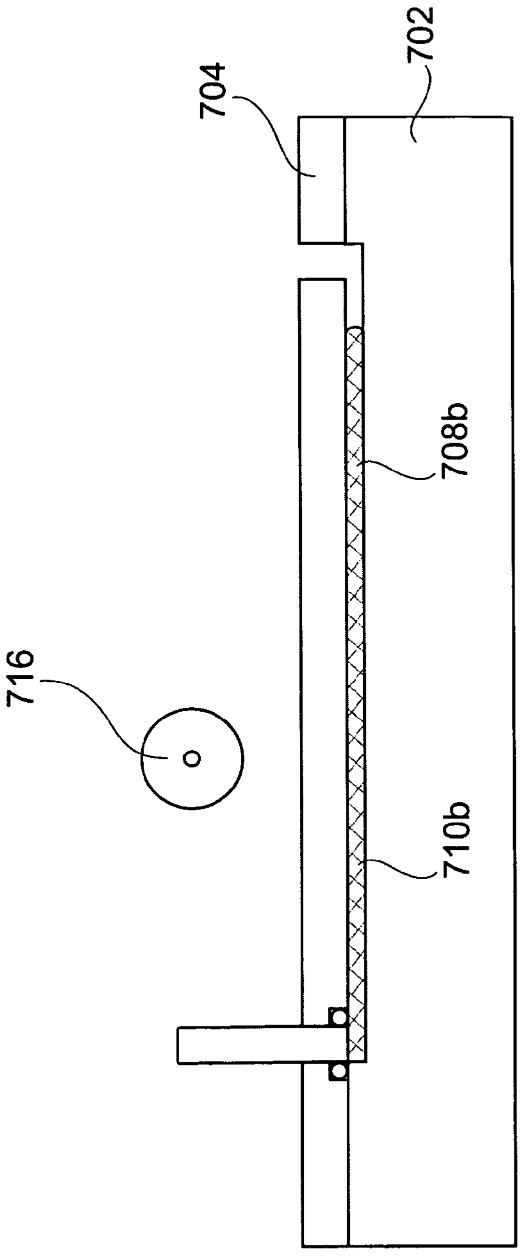
FIG. 10*d* illustrates the microfluidic device of FIG. 10*c* with the step of drawing the liquid sample from the sample capillary into the microfluidic network of the microfluidic device having been completed.
Figure 10E:
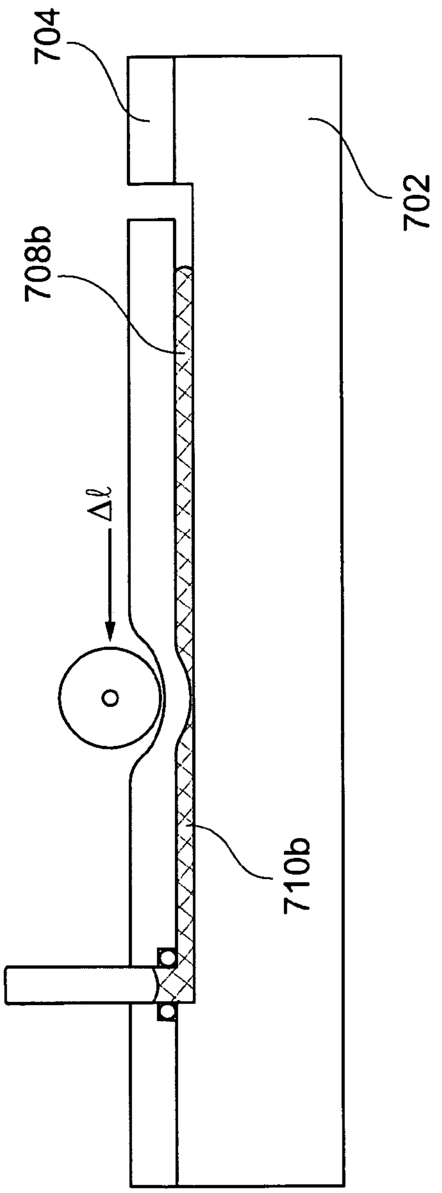
FIG. 10*e* illustrates the microfluidic device of FIG. 10*d* with a portion of the liquid sample being moved a distance Δ1 along a length of the microfluidic network.

As seen in FIG. 10*d*, substantially all (e.g., at least 70%, at least 80%, at least 90%, at least 95%, essentially all) of the volume V of liquid sample 737 is drawn into the microfluidic network. In an exemplary embodiment, at least 90% of volume V is drawn into the network.

Liquid sample within the microfluidic network enters each of channels 710*i* and reservoirs 708*i* and mobilizes the reagents within each reservoir to form a mixture. Typically, formation of the mixture is assisted causing bulk motion of the liquid sample within the microfluidic network. Such bulk motion is typically caused by compression and decompression of the microfluidic device to reduce an internal distance between substrates 702,704. The compression and decompression can be performed in a peristaltic fashion by repeated movements of at least one of the roller 716 and microfluidic device 700 with respect to the other.

In general, the total volume of the mixtures formed by the combination of reagents 735*i* in the N channels of device 700 includes at least about 70% (e.g., at least about 80%, at least about 90%, at least about 95%, essentially all) of the amount of liquid sample introduced to the device 700. In an exemplary embodiment the total volume of the mixtures formed by the combination of reagents 735*i* in the N channels of device 700 includes at least about 90% of the amount of liquid sample introduced to the device 700.

Within each mixture of the microfluidic device, particles, if present, combine with detectable label to form complexes. After a suitable incubation period to permit complex formation, the presence of complexes is detected. Each reagent 735*i* is typically configured to permit detection of a different analyte. Examples of detection of complexes is described in International Patent Application PCT/EP2006/068153, which is incorporated by reference in its entirety.

Figure 10F:
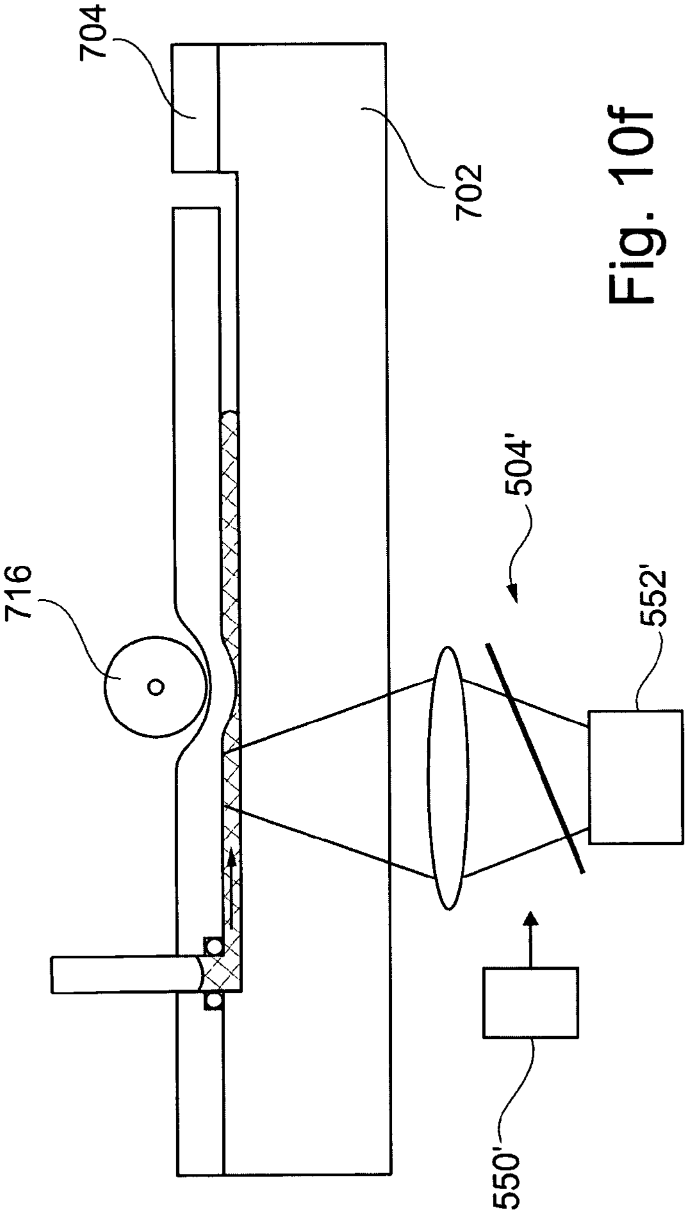
FIG. 10*f* illustrates the microfluidic device of FIG. 10*e* and detection of an analyte present within a portion of the liquid sample.

Referring to FIG. 10*f*, detection typically takes place within a subset of each mixture within the device. In general, detection can be performed within multiple different subsets of each mixture. For example, different subsets of each mixture can be moved through the detection zone by moving roller 716 in a compressed state to move a fresh portion of the mixture into each detection zone. This can be performed multiple times so that substantially all (e.g., at least 70%, at least 80%, at least 90%, at least 95%, essentially all) of each mixture can be subjected to detection. In this embodiment, detection is performed with roller 716 in a compressed state. Mixture that has already been subject to detection enters capillary 736, which acts as a waste container.

In some embodiments, detection is performed by scanning the device 700 with respect to the optical detector so that each detection sequentially comprises a different subset of the solution. This can be performed multiple times so that substantially all (e.g., at least 70%, at least 80%, at least 90%, at least 95%, essentially all) of each mixture can be subjected to detection. In this embodiment, detection is performed with roller 716 in a decompressed state.

Methods and devices for performing assays have been described. Examples of other embodiments are discussed next.

While inlet 106 has been described as an unobstructed opening, other configurations are possible. For example, an inlet may be configured with a syringe fitting (e.g., a gas-tight fitting) to receive a syringe. Alternatively, an inlet may be configured as a gasket through which a sample may be introduced by a needle. As another alternative, the inlet may be fitted with a one-way valve that allows sample to be introduced but not to exit. As another alternative, the inlet may be configured to receive a standard capillary (e.g., an end-to-end capillary such as a plastic capillary). The capillary may be anti-coagulant coated such as with heparin. Examples of suitable capillaries include 20 μl heparin coated capillaries available from Kabe Labortechnik (Nürnbrecht-Elsenroth, Deutschland; http://www.kabe-labortechnik.de/index.php?sprache=de&akt_seite=startseite_produkte.php).

While a microfluidic device has been described that fills by capillary action, other embodiments can be used. For example, system 500 can be designed to reduce an internal volume of the microfluidic network prior to application of the sample to the inlet. When the sample is applied, the internal volume is increased thereby drawing the sample in. Such a volume decrease can be accomplished with, for example, compression roller 516. For example, microfluidic device may be received within housing 500 so that damped spring 514 of translation actuator 512 is in a compressed state. Compression roller 516 is positioned to compress device 100 at a location corresponding to reservoir 108. This compression reduces an internal volume of reservoir 108. The volume reduction is about as great as (e.g., at least about 25% greater than, at least 50% greater than) the volume of sample to be received within device 100. With reservoir 108 in the compressed state, a volume of sample is applied to inlet 106 of device 100. Compression roller 516 is retracted away from inlet 106 toward an opposite end 137 of device 100. As roller 516 moves away from reservoir 108, the reservoir decompresses thereby increasing the internal volume of the microfluidic network. The volume increase creates a vacuum that sucks the sample into the device.

While microfluidic devices having an open capillary channel have been described, other embodiments can be used. For example, the channel may include a medium occupying at least some (e.g., most or all) of the cross section of the channel along at least a portion of its length. Typically, the medium is one which to multiple probe compounds can be immobilized to define respective spaced apart test zones (e.g., capture volumes), each having capture sites disposed in three dimensions. Pores or voids in the medium permit liquid to permeate along the channel (e.g., by capillary action). Liquid movement along the channel may be assisted by or induced by, for example, generating a vacuum within the channel as described above. Typically, probe compounds are immobilized with respect to the porous medium to define spaced-apart test zones along the channel. Interaction of analytes with probe compounds of the test zones can be determined sequentially as described for test zones **112*i* of device 100**. Because each test zone is disposed in three dimensions, reducing the distance between the opposed inner surfaces of the channel decreases the capture volume occupied by the immobilized probe compounds of the test zone. Optical detection is performed with the test zone in the reduced volume (i.e., reduced distance) state.

Figure 7:
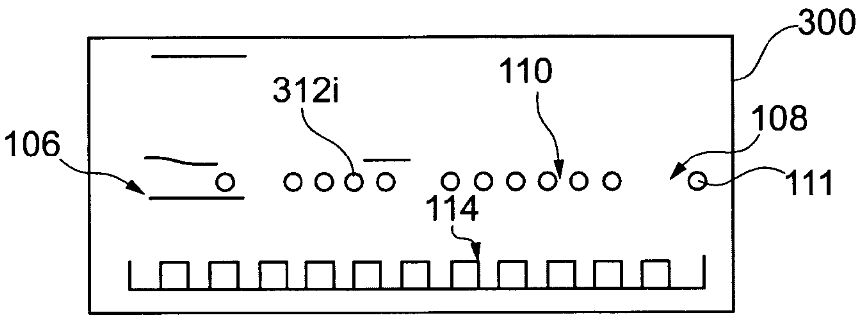
FIG. 7 illustrates a microfluidic device.

While test zones **112*i* have been shown as elongate, other configurations are possible. For example, referring to FIG. 7, a microfluidic device 300 includes multiple test zones 312*i* each having a generally circular configuration. Other than a difference in shape, test zones 312*i* may be identical to test zones 112*i* of device 100. Other than a difference in test zones, devices 100 and 300** can be identical.

While a method for forming test zones **112*i* has been described as moving distal tip 404 and substrate 102 from an initial separation d1 (FIG. 3*b*) to an adjacent separation d2 (FIG. 3*c*) and to an intermediate separation d3 (FIG. 3*d*) prior to initiating lateral movement of distal tip 404 and substrate 102 (FIG. 3*f*), other embodiments can be performed. For example, distal tip 404 and substrate 102 can be moved laterally with tip 404 and substrate 102 in the adjacent separation d2. In this embodiment, separation d2** is typically greater than zero.

While a method for forming test zones **112*i* has been described as including a step of maintaining distal tip 404 and substrate 102 at an intermediate separation d3 for an incubation time until only a remaining portion 402' of reagent solution 402 remains, other embodiments can be performed. For example, lateral movement of distal tip 404 and substrate 102 can begin immediately as distal tip 404 and substrate 102 are moved from adjacent separation d2 (FIG. 3*c*) to separation d3 (FIG. 3*d***). In other words, the incubation time may be indistinguishable from zero. As another example, during the incubation, evaporating reagent solution may be replaced with additional reagent solution introduced to the capillary tip. Accordingly, the total amount of reagent at the capillary tip increases during the incubation.

While a method for forming test zones **112*i* has been described as including an incubation time with distal tip 404 and substrate 102 maintained at a separation d3, other embodiments can be performed. For example, separation d3 can vary during the incubation time. For example, tip 404 can be oscillated laterally and or vertically relative to substrate 102 during the incubation time. Alternatively or in combination, tip 404 can be oscillated laterally and or vertically relative to substrate 102** during lateral movement. Such oscillation can enhance transport of probe molecules to the first substrate during incubation or lateral motion.

While a method for forming test zones **112*i*** has been described as using a capillary dispenser, other dispensers may be used. For example, material may be dispensed from a solid dispenser (e.g., a solid rod).

While a method for forming test zones **112*i* has been described as introducing an amount of reagent solution to a distal tip of a capillary of a capillary spotter (FIG. 3*b*) and bringing the tip and a substrate to a smaller separation d2 so that reagent solution 402 contacts a location of substrate 102**, other embodiments can be performed. For example, reagent solution may be introduced to the distal tip only after the distal tip and substrate are brought to a smaller separation (e.g., after the distal tip is contacted with the substrate).

While a method and microfluidic device reader for sequentially reducing a distance between inner surfaces of a channel having been described, other configurations are possible. For example, a microfluidic device reader may be configured to simultaneously reduce a distance between inner surfaces along most (e.g., substantially all or all) of a channel. Subsequently, the reader translates the detection zone of a detector along the channel so that different test zones are read sequentially.

While a microfluidic device having a first relative rigid substrate and a second relatively flexible substrate has been described, other embodiments can be used. For example, the substrates define both opposed inner surfaces of a channel can be flexible. In such embodiments, a portion of the optical detector can form part of the compression system. For example, the microfluidic device may translate between a compression roller and an optic of the detector.

While a reference pattern has been described as providing information related to spatial properties of test zones of a microfluidic device, the reference pattern may provide additional or alternative information. For example, a reference pattern can provide information related to physiochemical properties of test zones of a microfluidic device. Such properties include analytes for which the test zones are configured to assay. Other properties include the identity and properties of reagents stored on the device and date information (e.g., the expiration date) of the device.

While a reference pattern including magnetic indicia has been described, other indicia can be used. For example, the indicia may be formed of regions having different optical density or reflectance as compared to the surrounding material. The reference pattern reader is an optical reader typically configured to read the indicia by transmittance or reflectance.

In other embodiments, the first substrate can include a channel formed, for example, via injection molding. The channel has a first dimension (length) substantially greater than its second and third dimensions (i.e., width and depth). The channel can have a cross section that is rectangular, V-shaped (triangular), U-shaped, or other shape. In some embodiments, the shape and/or dimensions of the cross section of the channel can vary along the length of the channel. The second substrate can be affixed to the first substrate by an adhesive. The second substrate can be formed of, for example, a transparent tape. The second substrate (e.g., the tape) can have a mechanical stiffness, such that mechanical contact with an outer surface of the second substrate (e.g., the tape) does not substantially deform the inner surface of the second substrate.

In certain embodiments, the channel may be defined by the inner surface of a tube, a pipe a capillary or the like. The channel can have a cross section that is rectangular, V-shaped (triangular), or other shape. In some embodiments, the shape and/or dimensions of the cross section of the channel can vary along the length of the channel A portion of the channel may be optically transparent.

In some embodiments, the channel includes one or more reference and/or alignment marks, such as defined structures or immobilized molecules configured to be detectable with the detection system used for the assay. The alignment marks can include, for instance, immobilized fluorescent beads, immobilized fluorescent polymers, proteins, nucleic acids and the like. Alignment marks also can include physical structures like microstructures and the like.

The device can be configured to form a fluid circuit after having introduced the sample to the channel. The fluid circuit encloses the liquid sample in an endless loop. When the liquid sample is enclosed in the fluid circuit, and the volume of the liquid sample is less than the total volume of the fluid circuit, the remaining volume in the fluid circuit can be occupied by a transport fluid. The transport fluid can be a liquid that is substantially immiscible with the sample liquid (e.g., by virtue of hydrophilicity/hydrophobicity, or differences in density). The transport fluid can be a gas, such as, for example, air. Typically, the liquid sample will be present in the fluid circuit in a continuous slug.

A portion of the fluid circuit includes a compressible zone. The compressible zone can be a length of the fluid circuit along which at least one wall of the circuit is compressible or deformable. When a localized compressive force is applied to the compressible zone, the wall deforms. Under a sufficient force, the wall can be compressed to a degree that interrupts the fluid circuit. Most commonly, the fluid circuit will be interrupted at a predetermined location, where the channel is filled with the transport fluid.

Once the fluid circuit has been interrupted, the location of the fluid sample within the fluid circuit can be manipulated by moving the location of the interruption with respect to the rest of the fluid circuit. Moving the interruption decreases the volume of the transport fluid to one side of the interruption, with a corresponding increase in volume of the transport fluid on the other side of the interruption. The changes in volume result in a differential pressure on the ends of the liquid sample (i.e., where the liquid sample and transport fluid meet). The liquid sample responds by moving within the fluid circuit to equalize the pressures.

One or more test zones can be spaced apart along the channel. Typically, each assay includes interaction of the probe compound with the respective analyte or with a respective complex including the analyte and a reagent (e.g., an optical label).

Location of the sample within the channel can be controlled by an actuator or roller configured to subject a portion of the compressible zone to a localized compressive force. The microfluidic device is translated relative to the actuator or roller so that the sample travels to a desired location within the channel. Alternatively, the roller can be moved while the device remains stationary.

Figure 12:
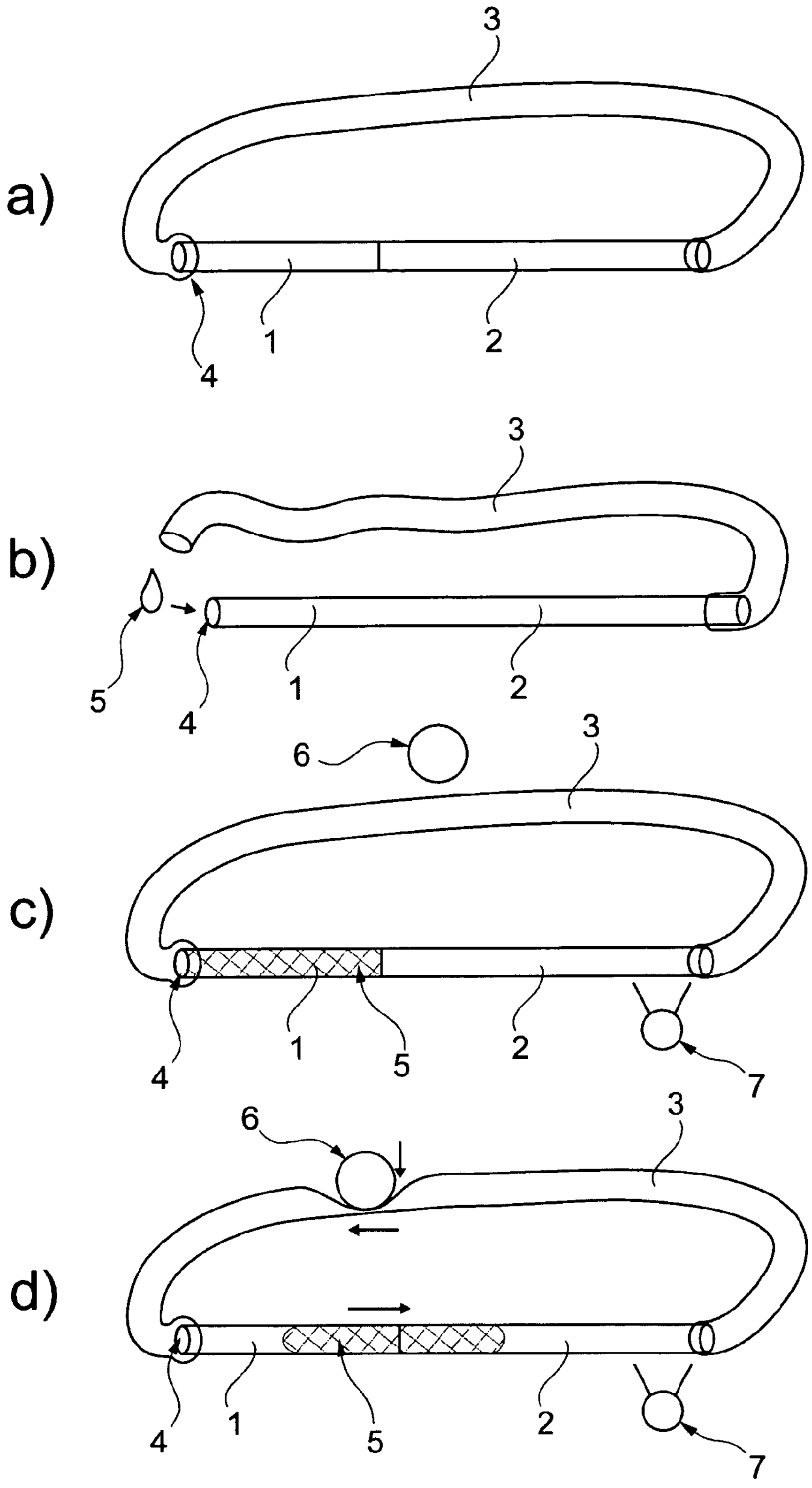
FIGS. 12A-12D show a schematic depiction of a fluid circuit.

FIG. 12A illustrates fluid circuit 10 in a closed state. Fluid circuit 10 includes first zone 1, microfluidic channel 2, second zone 3, and inlet 4. In the closed state, second zone 3 is tightly connected to inlet 4. FIG. 12B shows fluid circuit 10 in an open state and ready to accept liquid sample 5 at inlet 4. After liquid sample 5 is contacted to inlet 4, capillary action draws liquid sample 5 into first zone 1. FIGS. 12C-12D shows the fluid circuit in a closed state after the sample has been applied. Roller 6 is positioned with respect to second zone 3 such that the second zone is either in an uncompressed state (as in FIG. 12C) or in a compressed state (as in FIG. 12D). The location of liquid sample 5 within fluid circuit 10 can be adjusted by positioning roller 6 such that second zone 3 is in a compressed state, and while maintaining the compressed state, moving roller 6 relative to second zone 3 (illustrated by arrows in FIG. 12D). Because the fluid circuit is closed, the movement of roller 6 creates a differential pressure on either side of the roller; the differential pressure induces movement of liquid sample, thereby restoring equal pressures. The fluid circuit can be configured to work in a cartridge. In certain examples, the fluid circuit can have a microfluidic flow path capable of compression through deformation, a microfluidic channel including a detection region, and a sealing member that can reversibly or irreversibly form a closed fluid circuit.

Figure 13:
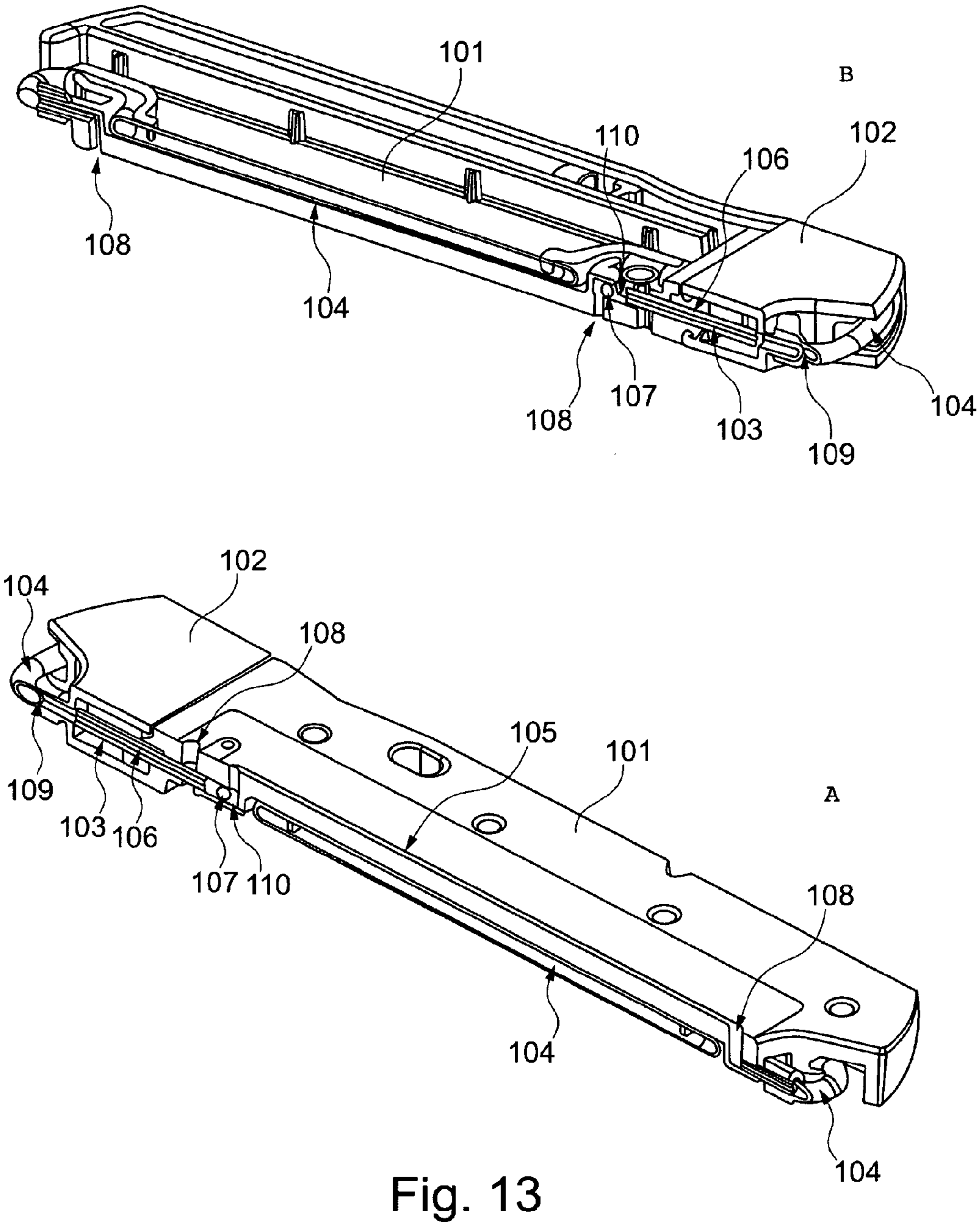
FIGS. 13A-13B show cutaway views of a cartridge having a fluid circuit.

FIGS. 13A-13B show a cutaway views of an exemplary cartridge 100. Cartridge 100 includes substrate 101, cap 102, and a fluid circuit including first zone 103, conduits 108, channel 105, second zone 104, and inlet/tight connection 109. Channel 105 can be covered by an at least partially optically transmissible layer. First zone 103 can be e.g. a capillary, selected to hold a desired sample volume (e.g., 1 μL to 20 μL, 2 to 10 μL, or about 5 μL). The capillary can be coated with an anticoagulant on its inner surface. Inlet 109 of the capillary is configured to receive the sample 106. In some embodiments, the exit of the capillary opens out to a reaction chamber 110 with a predetermined volume of, e.g., about 5 µL, 10 µL or 20 µL. In some embodiments, reaction chamber 110 includes a reagent pellet 107. The reagent pellet can include antibodies labelled with a fluorescent dye and having an affinity for antigens to be detected within the sample. For instance, for detecting the number of T-helper-cells in a liquid sample the reagent pellet can include an anti-CD4+-antibody labelled with a first fluorescent dye (such as phycoerythrine) and an anti-CD3+-antibody labelled with a second fluorescent dye such as (phycoerythrine-Cy5), salts and stabilizing reagents etc. In some embodiments, the inner surface of the first zone is covered with reagents necessary for processing the sample. An exemplary assay for detecting particles such as cells in a liquid sample is described in, for example, in WO 2007/051861, which is incorporated by reference in its entirety. Conduit 108 in fluid communication with the reaction chamber 110 connects the reaction chamber with the first end of channel 105. As described in WO 2007/051861, detection can take place in the channel. Thus, the channel is at least partially optically transparent. For example, channel 105 can be covered by an at least partially optically transmissible layer. The second end of channel 105 is connected to a first end of second zone 104 via conduit 108. The second zone is at least partially flexible so that the inner diameter of the second zone can be reduced to zero. For example, the second zone can be an elastic silicone tube or the like. A second end of the second zone is mounted into a cap 102 which is adapted to be applied to the substrate and to support the second zone. By opening the cap, tight connection 109 between the first and the second zone is opened, by closing the cap, the tight connection 109 between the first and the second zone is closed.

In shipping condition the device can be closed, i.e., the second zone forms a tight connection with the first zone at connection 109. Alternatively, the device can be shipped in an open state. In some embodiments, the device includes (e.g., for safety purposes) a mechanism configured to prevent the cartridge from becoming opened after it is first closed. Connection 109 is closed when a sealing member in cap 102 forms a fluid-tight connection with end of capillary 103. In operation, the user opens the cap, thereby opening the first zone on its first end. The user contacts the open end of the first zone with the sample liquid, e.g., a blood drop such as produced by a finger stick. Thus, capillary 103 fills with the sample. The user closes the cap thereby closing connection 109 between the first and the second zone. At this point, the fluid circuit includes a contiguous, predetermined volume of sample liquid, the reagent pellet, and a contiguous volume of transport fluid (e.g., air) within the reaction chamber, conduits, channel and second zone. The user puts the device into the machine designed for operating the device. The machine includes an actuator configured to compress the second zone, a detector, and a controller. The actuator compresses the second zone, reducing its diameter at the compression point to zero. When the device and the actuator are moved relative to each other while in a compressed state, the pressure in the transport fluid will increase on the one end of the sample volume while it will decrease on the other end of the sample volume. The sample volume will move within the fluid circuit until the pressure on each end of the sample volume is equal.

Channel 105 can be hydrophobic, such that the sample will not move into channel 105 without application of an external force. In some embodiments, the walls in the vicinity of reagent pellet 107 can also be hydrophobic. When using hydrophilic materials the long-term stability of the reagent pellet can be worse compared to a hydrophobic material.

In one embodiment, the actuator is fixed within the machine and the device is moved relative to the means for compressing. As described in WO 2007/051861, the actuator is e.g. a roller.

The device can be moved within the machine such that the sample will move into the reaction chamber thereby dissolving the reagent pellet in this chamber. The antibodies will bind to the respective antigens present in the sample. Depending on the type of sample, antigens may be located on particles suspended in the sample liquid (e.g., on cell surfaces in a blood sample). Because the antibodies are labelled (e.g., with a fluorescent dye), once bound to their respective antigens, the antigens become labelled as well. See, e.g., WO 2007/051861. By further moving the device relative to the machine in the same direction the sample is moved into the channel. Once the channel is filled, detection takes place.

Desirably, the detector is small, inexpensive, and versatile; that is, it is adaptable to other applications than solely the use described here. The detector can be a fluorescence microscope, preferably one that has very small outer dimensions and a small height with respect to the cartridge. The detector can be capable of imaging objects with a size≥5 µm and is configured to detect signals of the wavelength which are emitted by the fluorescent dyes used in the assay. The light source can be a high-power LED emitting light in a spectrum which is suitable to excite the fluorescent dyes used in the assay. If different dyes are used, e.g. at least two different dyes emitting light at two different wave lengths, detection should be possible at each of at least two different wavelengths. The detector can include a focus mechanism and a camera.

Usually, very strong light sources are used for fluorescence microscopy, because to have almost parallel light beams, only a small portion of the emitted light is used (solid angle ~2°). By using a condenser lens and detector lens that collects a greater portion of light emitted from the source, a less powerful source (e.g., an LED) can be used. Fluorescence microscopy traditionally places a very high value on optical fidelity; as such, the field has taught away from high solid angles for condenser lenses. Indeed, the field has tended to teach relatively heavy, bulky, and complex optical systems for achieving high optical fidelity.

Figure 14A:
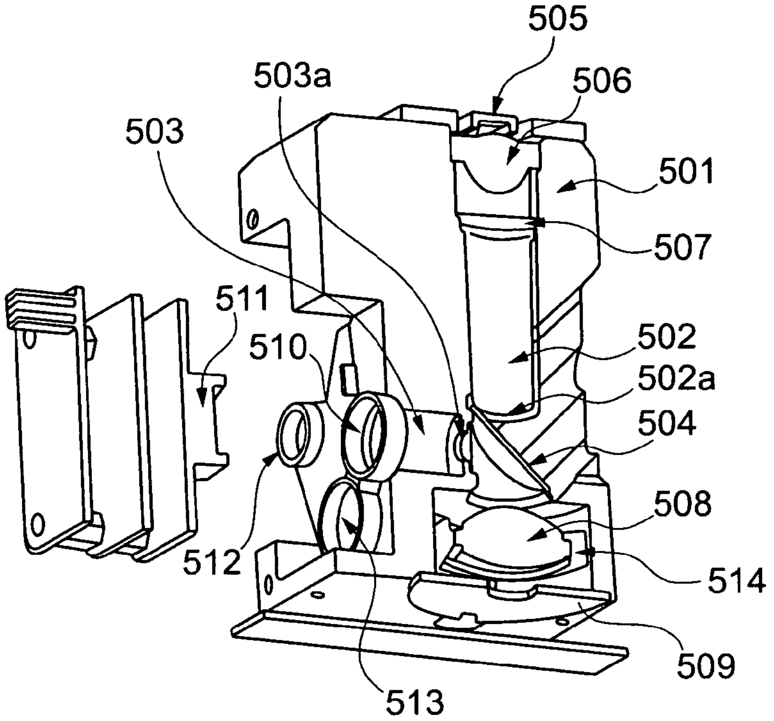
FIGS. 14A-14B show cutaway views of a fluorescence detector.
Figure 14B:
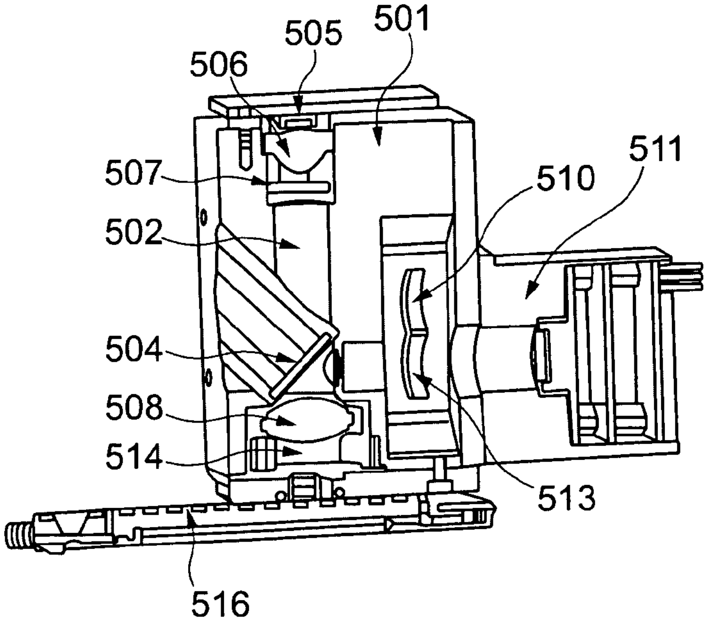

With reference to FIG. 14, an exemplary detector 500 includes a main body 501 which includes a first optical path 502 and a second optical path 503. In certain examples, each of the optical paths, independently, can have a generally cylindrical shape or other suitable configuration. First optical path 502 represents the excitation optical path; second optical 503 represents the detection optical path.

First optical path 502 connects light source 505 with cartridge 516. Light source 505 can be a high power LED (such as a Platinum Dragon® LED (Osram)) with emission wavelengths of 455 nm, 470 nm and 528 nm and a viewing angle of 120° (Lambertian emitter). When using fluorescent dyes the light source is selected according to the excitation wavelength of the fluorescent dyes which are used in the assay. E.g., when using phycoerythrine and phycoerythrine-Cy5 the light source is selected to emit light with a wavelength of around 520 nm while for the use of phycoerythrine and PerCP the light source is selected to emit light around 480 nm. Condenser lens 506 (e.g., made from topaz, refraction index 1.533) condenses the light emitted by the LED into the first optical path 502. Aperture 502*a* is configured to allow a maximum solid angle of 13.5° or less to illuminate dichroic mirror 504. Optical path 502 also includes a band pass filter 507 (excitation filter), allowing light with a wavelength between 505 nm and 530 nm to pass. Thus, the remaining excitation wavelength would be around 528 nm.

Optical path 503 connects the CMOS camera with the object 516 via dichroic mirror 504 and is configured at an angle (shown as 90° in FIG. 14) relative to optical path 502. Optical path 503 also includes a first emission filter 510. In some embodiments, filter 510 is mounted to a filter changer 512. Filter changer 512 may include additional emission filter(s), e.g. a filter 513. Emission filters 510 and 513 can be chosen with regard to a predetermined set of emission wavelengths, e.g., the emission wavelengths of the fluorescent dye(s) used for labelling reagents in the cartridge. For example, filters 510 and 513 may be selected to pass light with wavelengths of 590 nm and 685 nm, respectively, corresponding to the emission wavelengths of phycoerythrine and phycoerythrine-Cy5. Optical path 503 includes an aperture 503*a* configured to allow a maximum solid angle of 13.5° on dichroic mirror 504.

Dichroic mirror 504 is configured to separate detection optical path 503 from excitation optical path 502. In some embodiments it is a short pass dichroic mirror allowing light with a wavelength<=568 nm to pass while light with a wavelength>568 nm is reflected. Thus, dichroic mirror 504 allows the light from the excitation optical path to pass while the light from the object 516 is reflected into the detection optical path. Again, physical properties of dichroic mirror 504 are selected according to the labels (e.g., the fluorescent dyes) which are used in the assay.

In some embodiments, the detector further includes a focusing mechanism 514 allowing varying the distance of detection lens 508 and object continuously by 5 mm or less, e.g. by 1 or 2 mm.

In some embodiments, detection lens 508 is configured to have a detection optical aperture of 0.4 or less, e.g. 0.2 and a excitation optical aperture of 0.5 or less, e.g. 0.4.

The detector also may include a digital imaging device such as an 8-bit grey value CMOS camera with a resolution of e.g. 640×480 pixels. In other embodiments, the digital imaging device may have a higher resolution and/or may be a colour CMOS camera.

In some embodiments, the reproduction scale of the detection system is between 1:1 and 1:10, e.g. 1:3, 1:4 or 1:5.

In some embodiments, the distance between the object 516 and the detection lens 508 is between 2 mm and 20 mm, e.g. 8 mm, 9 mm or 10 mm.

Figure 15:
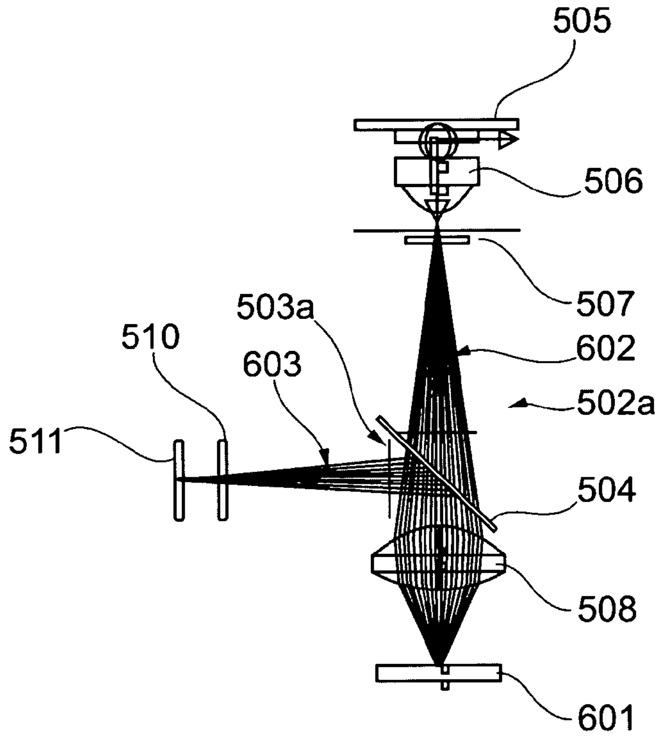
FIG. 15 shows a scheme of optical path of a detector.

With reference to FIG. 15, in operation the light emitted from the light source 505 is condensed via lens 506 and filtered via excitation filter 507. It passes aperture 502*a*, dichroic mirror 504, detection lens 508, aperture 509 and excites the object 601. In some embodiments, the object 516 is the channel filled with the sample liquid, e.g. blood, the liquid including a number of particles, e.g. T-helper cells to be detected. The particles may be labelled with one or more fluorescent dye coupled antibodies. In other embodiments, the object is a channel including target molecules labelled with one or more fluorescent dyes and bound to probe molecules or an array of probe molecules immobilized on one of the channel's surfaces. The dyes fluoresce under the influence of the excitation light from the LED. The light emitted from the fluorescent dyes passes aperture 509, detection lens 508 and is reflected via dichroic mirror 504 into the detection optical path 503. There it passes detection filter 510 (or 513, depending of the position of filter changer 512) adapted to allow the passage of light of a wavelength of the light emitted from the fluorescent dye. After the light has passed the filter, it is collected by the CMOS chip of the attached CMOS camera 511.

Figure 16A:
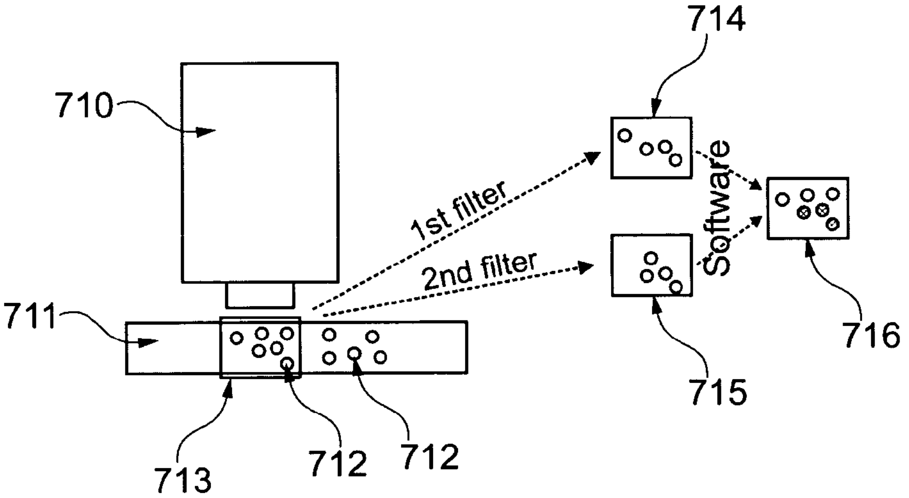
FIGS. 16A-16B show depictions of a cell counting assay using a fluorescence detector.
Figure 16B:
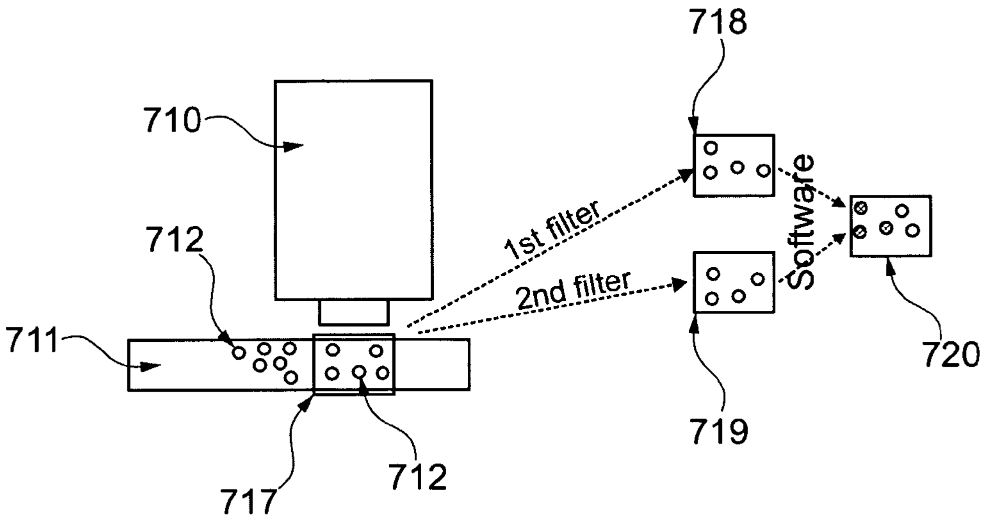

FIGS. 16A-16B illustrates how the detector can be used for detecting, e.g. the number of T-helper cells present in a blood sample. Details for the device and the reaction can be found above and in WO 2007/051861 which is incorporated herein by reference. In the example discussed, the cartridge is prepared with two labelled antibodies: phycoerythrine-labelled anti CD4 antibodies and phycoerythrine-Cy5-labelled anti-CD3 antibodies. Since T-helper cells show both antigens on their surface, T-helper cells will be labelled with both fluorescent dyes. Other cells, showing only one of the both antigens on their surfaces, may be also present in the sample. These cells will be labelled only with the according fluorescent dye.

After reaction with the respective fluorescent dye labelled antibodies, the liquid sample comprising fluorescing cells 712 is moved into the detection channel 711. At a first position (FIG. 16A) the detector 710 detects a first image 714 representing a view on a portion 713 of channel 711. Portion 713 represents a predetermined volume of the sample, e.g. 100 mL. Image 714 is taken with a first filter which is configured to allow light emitted by phycoerythrine-labelled anti CD4+ antibodies present in the sample and to block light emitted by phycoerythrine-Cy5-anti-CD3+ antibodies. A second image 715 of the same position is taken using a second filter which is configured to allow phycoerythrine-Cy5-anti-CD3+ antibodies and to block light emitted by phycoerythrine-labelled anti CD4+. Images 714 and 715 may show a different number of signals within portion 713. Additionally, due to aberrations in the optical system, both images 714 and 715 might be out of alignment relative to each other.

Software (e.g. Iconoclust by Clondiag) can be used to align both images 714 and 715, e.g. by using alignment marks in the channel (not shown) or by analyzing the relationships between signals which are present in both of the pictures. Additionally, the software identifies and marks the signals which have been detected in both pictures (716). In FIG. 16A, three signals were identified to be present in both figures. That means that 3 cells with both antigens were found in portion 713. The results may be displayed, used for further calculations or statistics or may be stored for further processing.

Detector 710 and channel 711 are moved relative to each other to view another portion 717 of channel 711 (FIG. 16B) and the detection procedure is repeated. Images 718 and 719 are recorded, using the first and second filters respectively. The software identifies and marks the signals which have been detected in both pictures (720).

Detection may be repeated in the additional portions of the detection channel, resulting in a set of values representing the number of cells in each of the portions. The number of cells present in the sample, as well as corresponding statistical parameters may be calculated from this set of values. For example, an average of three cells per 100 mL corresponds to a total amount of 150 cells in a sample volume of 5 μL.

Figure 17:
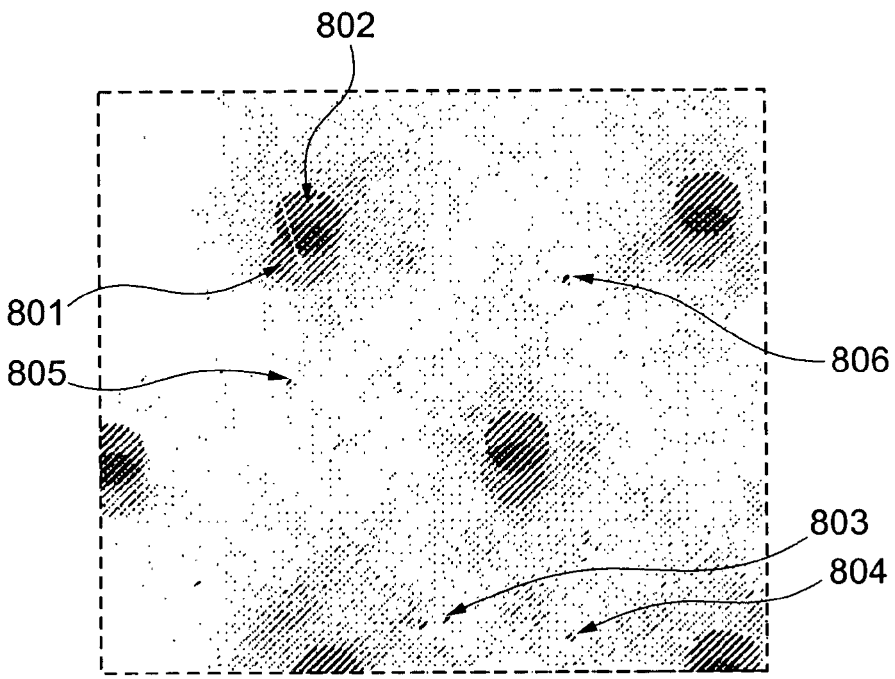
FIG. 17 shows an overlay of two images derived from a cell counting assay using a fluorescence detector.

FIG. 17 shows an overlay of two images detected during a T-cell counting experiment using blood as liquid sample. Both images are detected at the same location of the channel (e.g. like images 714 and 715 in FIG. 5) using two different detection filters. 801 and 802 represent one alignment mark imaged using two different detection filters. The dislocation between both images can clearly be detected and corrected by using the marks. 803 and 804 represent a single cell which is dislocated by the same distance like the alignment marks 801 and 802. Since this cell is present in both of the images, it can be determined that this cell is labelled with both antibodies and thus is a T-helper-cell. 805 represents a cell which is only detectable in one of the both images of the overlay. Thus it can be derived that this cell does not show both antigens on its surface and therefore is not a T-helper-cell. Other blood cells can also be seen in the images. Since they are not labelled with any fluorescent antibodies, they only can be seen as a shadow (806).

Other embodiments are within the scope of the claims.

The invention claimed is:

1. A device for detecting an analyte, comprising:

a cartridge having:

a microfluidic channel including an inlet and a detection region in fluid communication with the inlet;

a microfluidic flow path having an at least partially deformable wall and in fluid communication with the detection region of the channel; and a cap having: a sealing member configured to seal with the inlet and form a fluid circuit including the inlet, the microfluidic channel and the microfluidic flow path, wherein the cap and cartridge are configured to close irreversibly after forming the fluid circuit.

2. The device of claim 1, wherein the cap is flexibly attached to the cartridge.

3. The device of claim 1, wherein the cap and cartridge are configured to engage in a first relative position such that the cap can be removed and to engage in a second relative position such that the cap is irreversibly closed after forming the fluid circuit.

4. The device of claim 1, wherein the detection region is bounded by at least one surface of the cartridge and at least one surface of a lid.

5. The device of claim 4, wherein the lid includes a transparent film over the detection region.

6. The device of claim 5, wherein the lid is adhesively affixed to the cartridge.

7. A device for detecting an analyte, comprising:

a cartridge having:

a microfluidic channel including a capillary inlet having an anticoagulant on an inner surface, a chamber including a reagent, and a detection region in fluid communication with the inlet;

a microfluidic flow path having an at least partially deformable wall and in fluid communication with the detection region of the channel; and a cap having:

a sealing member configured to seal with the inlet and form a fluid circuit including the inlet, the microfluidic channel and the microfluidic flow path, wherein the cap and cartridge are configured to close irreversibly after forming the fluid circuit.

8. A device for detecting an analyte, comprising:

a cartridge having:

a microfluidic channel including an inlet and a detection region in fluid communication with the inlet;

a microfluidic flow path having an at least partially deformable wall and in fluid communication with the detection region of the channel; and a cap having: a sealing member configured to seal with the inlet and form a fluid circuit including the inlet, the microfluidic channel and the microfluidic flow path, wherein the cap is flexibly attached to the cartridge.

9. The device of claim 8, wherein the cap and cartridge are configured to close irreversibly after forming the fluid circuit.

10. The device of claim 8, wherein the cap and cartridge are configured to engage in a first relative position such that the cap can be removed and to engage in a second relative position such that the cap is irreversibly closed after forming the fluid circuit.

11. The device of claim 8, wherein the detection region is bounded by at least one surface of the cartridge and at least one surface of a lid.

12. The device of claim 11, wherein the lid includes a transparent film over the detection region.

13. The device of claim 12, wherein the lid is adhesively affixed to the cartridge.

14. A device for detecting an analyte, comprising:

a cartridge having:

a microfluidic channel including an inlet and a detection region in fluid communication with the inlet;

a microfluidic flow path having an at least partially deformable wall and in fluid communication with the detection region of the channel; and a cap having: a sealing member configured to seal with the inlet and form a fluid circuit including the inlet, the microfluidic channel and the microfluidic flow path, wherein the detection region is bounded by at least one surface of the cartridge and at least one surface of a lid, the lid includes a transparent film over the detection region, and the lid is adhesively affixed to the cartridge.

15. The device of claim 14, wherein the cap and cartridge are configured to close irreversibly after forming the fluid circuit.

16. The device of claim 14, wherein the cap is flexibly attached to the cartridge.

17. The device of claim 14, wherein the cap and cartridge are configured to engage in a first relative position such that the cap can be removed and to engage in a second relative position such that the cap is irreversibly closed after forming the fluid circuit.

18. A device for detecting an analyte, comprising:

a cartridge having:

a microfluidic channel including a capillary inlet having an anticoagulant on an inner surface, a chamber including a reagent, and a detection region in fluid communication with the inlet;

a microfluidic flow path having an at least partially deformable wall and in fluid communication with the detection region of the channel; and a cap having:

a sealing member configured to seal with the inlet and form a fluid circuit including the inlet, the microfluidic channel and the microfluidic flow path, wherein the cap is flexibly attached to the cartridge.

* * * * *